United States Patent
Mohammadiamirabad et al.

(10) Patent No.: US 12,241,051 B2
(45) Date of Patent: Mar. 4, 2025

(54) METHOD FOR FORMING A POROUS CELL SUBSTRATE

(71) Applicant: Upside Foods, Inc., Berkeley, CA (US)

(72) Inventors: Leila Mohammadiamirabad, Madison, WI (US); John Pattison, Madison, WI (US); Ian Johnson, Madison, WI (US); Vaishnavee Patil, Madison, WI (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

(21) Appl. No.: 18/351,345

(22) Filed: Jul. 12, 2023

(65) Prior Publication Data

US 2024/0018458 A1 Jan. 18, 2024

Related U.S. Application Data

(60) Provisional application No. 63/368,222, filed on Jul. 12, 2022.

(51) Int. Cl.
C12M 1/12 (2006.01)
C12M 1/26 (2006.01)

(52) U.S. Cl.
CPC ............ *C12M 25/12* (2013.01); *C12M 25/14* (2013.01); *C12M 33/04* (2013.01)

(58) Field of Classification Search
None
See application file for complete search history.

(56) References Cited

PUBLICATIONS

Battiston et al. "Biomaterials in co-culture systems: Towards optimizing tissue integration and cell signaling within scaffolds" (2014) Biomaterials, vol. 35: 4465-4476. (Year: 2014).*
Xiang et al. "3D porous scaffolds from wheat glutenin for cultured meat applications" (Apr. 27, 2022) Biomaterials, vol. 285, 121543. (Year: 2022).*
Chang et al., Crustacean Hyperglycemic Hormone in the Lobster Nervous System: Localization and Release From Cells in the Subesophageal Ganglion and Thoracic Second Roots. The Journal of Comparative Neurology, 1999, vol. 414, p. 50-56.
Ianovici et al., 3D-printable plant protein-enriched scaffolds for cultivated meat development. Biomaterials. Mar. 24, 2022, vol. 284, 121487.
International Search Report and Written Opinion as received in PCT/US23/70071 dated Jan. 31, 2024.
Rommel et al., Functionalized Microgel Rods Interlinked into Soft Macroporous Structures for 3D Cell Culture. Adv. Sci. Jan. 14, 2022, vol. 9, 2103554. Abstract.
Jakob Schmid, et al. A Perfusion Bioreactor System for Cell Seeding and Oxygen-Controlled Cultivation of Three-Dimensional Cell Cultures, Tissue Engineering: part C, vol. 24, No. 10, 2008, Mary Ann Liebert, Inc., DOI: 10.1089/ten.tec.2018.0204, 585-595, Oct. 17, 2018, [Retrieved Oct. 10, 2023] from <https://www.liebertpub.com/doi/10.1089/ten.tec.2018.0204>.
Luis A. Solchaga, et al., A Rapid Seeding Technique for the Assembly of Large Cell/Scaffold Composite Constructs, National Institutes of Health, Tissue Eng. Jul. 2006, 12(7), 1851-1863 [Retrieved Aug. 10, 2023], from <https://www.ncbi.nlm.nih.gov/pmc/articles/PMC1858629/>.
Nifang Zhao, et al., Controlling ice formation on gradient wettability surface for high-performance bioinspired materials, Science Advances, vol. 6, No. 31, 14 Pages, Jul. 31, 2020, [Retrieved Aug. 10, 2023]. Retrieved from the internet <https://www.science.org/doi/full/10.1126/sciadv.abb4712>.
Therese Andersen, et al., 3D Cell Culture in Alginate Hydrolgels, Microarrays 2015, 4, 133-161; doi:10.3390/microarrays4020133, ISSN 2076-3905, Mar. 24, 2015.

* cited by examiner

*Primary Examiner* — Teresa E Knight
(74) *Attorney, Agent, or Firm* — Keller Preece PLLC

(57) ABSTRACT

This disclosure describes methods and apparatuses for creating or using a fibrous cell substrate that is formed in a mold using temperature and wettability gradients and that upon which cells can be grown. The disclosed method can include utilizing a temperature gradient and a wettability gradient within a mold to form a porous cell substrate. In particular, the temperature and wettability gradients control nucleation and growth of crystals within the cell substrate solution to form parallel layers of cell substrate. The crystals can be sublimated by freeze drying and the porous cell substrate is seeded. More specifically, the disclosed method includes using pressure and an increased cell mixture viscosity to seed cells deep within the cell substrate. This disclosure also describes an apparatus for forming the structured porous cell substrate.

19 Claims, 29 Drawing Sheets
(22 of 29 Drawing Sheet(s) Filed in Color)

METHOD FOR FORMING A POROUS CELL SUBSTRATE

CROSS-REFERENCE TO RELATED APPLICATIONS

The present application claims the benefit of, and priority to, U.S. Provisional Application No. 63/368,222, entitled "METHOD FOR FORMING A POROUS CELL SUBSTRATE," filed on Jul. 12, 2022. The aforementioned application is hereby incorporated by reference in its entirety.

BACKGROUND

As the world's population continues to grow, cell-based or cultured meat products for consumption have emerged as an attractive alternative (or supplement) to conventional meat from animals. For instance, cell-based, cultivated, or cultured meat represents a technology that could address the specific dietary needs of humans. Cell-based meat products can be prepared from a combination of cultivated adherent and suspension cells derived from a non-human animal. Because the cells for cell-based meat are made in a food cultivation facility, cell masses are often formed and shaped to mimic familiar forms of conventional meat.

In addition to addressing dietary needs, cell-based-meat products help alleviate several drawbacks linked to conventional meat products for humans, livestock, and the environment. For instance, conventional meat production involves controversial practices associated with animal husbandry, slaughter, and harvesting. Such harvesting can, for example, deplete fish, shellfish, or crustaceans from ecosystems of oceans or other bodies of water. Other drawbacks associated with harvested or slaughtered meat production include low conversion of caloric input to edible nutrients, microbial contamination of the product, emergence and propagation of veterinary and zoonotic diseases, relative natural resource requirements, and resultant industrial pollutants, such as greenhouse gas emissions and nitrogen waste streams.

Despite advances in creating cell-based-meat products, existing methods or systems for cultivating and processing cell-based-meat products face several shortcomings, such as challenges or failures to mimic the textures and flavors of slaughtered or harvested meat. In particular, existing methods or systems often produce cell-based-meat products with undesirable textures. Existing systems often grow cells that lack alignment, extracellular matrix, and are limited to two-dimensional structures in contrast with complex, three-dimensional, or unique structures of conventional cuts of meat, such as the meat harvested from shellfish. While cell-based-meat often readily mimics ground meat products, such as burgers, with processing, existing methods or systems fall short of creating cell-based-meat products with structure and texture comparable to conventional meat. As explained further below, existing methods and systems fail to mimic meats having highly organized tissue structures often found in shellfish, such as lobster, prawns, or scallops.

These, along with additional problems and issues exist in existing methods for cultivating cell-based-meat products.

BRIEF SUMMARY

This disclosure generally describes methods and apparatuses for creating or using a fibrous cell substrate that is formed in a mold using temperature and wettability gradients and that upon which cells can be grown. For example, the disclosed method includes securing a mold with a surface exhibiting a wettability gradient and filling the mold with a cell substrate solution. In some cases, the mold includes a metal surface with a coating creating the wettability gradient, a plastic cover, and a solution inlet as parts of an apparatus. Having filled the mold, the disclosed method further cools the mold's surface to both freeze the cell substrate solution and create a temperature gradient that controls or facilitates the direction of crystal nucleation. After removing the frozen cell substrate from the mold, the method further includes freeze drying the frozen cell substrate to sublimate the nucleated crystals. The resulting cell substrate forms a highly organized scaffold having a fibrous porous structure.

In addition or in the alternative to creating the cell substrate, cells may be seeded throughout the cell substrate. In one example, the disclosed method comprises suspending cells in an alginate solution to increase the viscosity of the cell mixture. The cell mixture is subsequently pressed through the cell substrate. The higher viscosity increases the likelihood that cells adhere to the cell substrate rather than passing through the pores. Cells may be grown within the cell substrate into a cell-based-meat product.

Additional features and advantages of one or more embodiments of the present disclosure will be set forth in the description that follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various embodiments will be described and explained with additional specificity and detail through the use of the accompanying drawings, which are summarized below.

DETAILED DESCRIPTION

Figure 1:
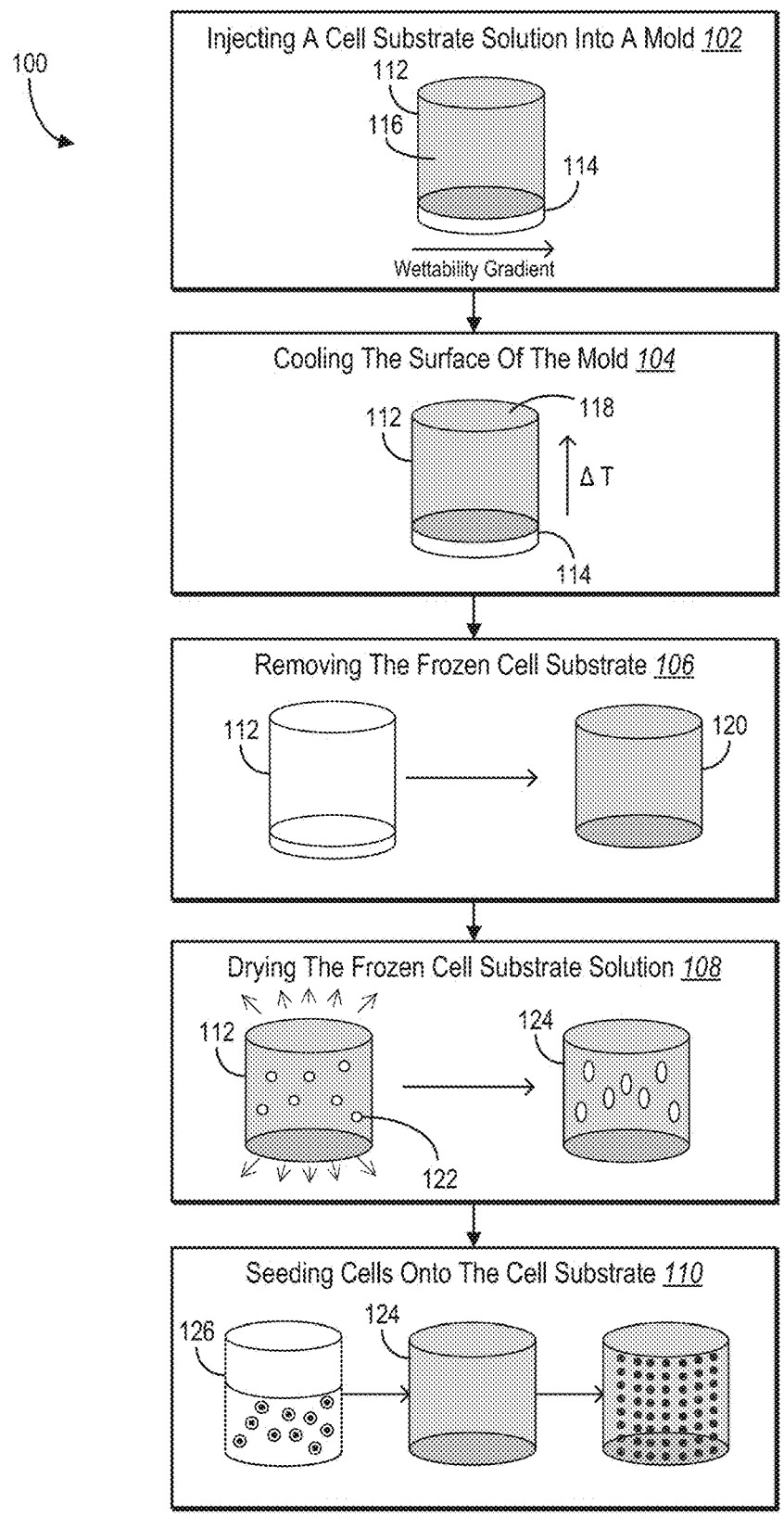
FIG. 1 illustrates an overview diagram of forming and seeding a structured porous cell substrate in accordance with one or more embodiments of the present disclosure.

This disclosure describes one or more embodiments of a method and apparatus for forming and seeding a fibrous cell substrate having a structure more similar to harvested or slaughtered meat than existing cell-growing substrates. In one or more embodiments, the disclosed method includes securing a mold with a surface having a wettability gradient. The disclosed method includes injecting a cell substrate solution into the mold and cooling the surface of the mold to create a temperature gradient across the mold's surface. The combination of the wettability gradient and the temperature gradient creates an organized nucleation and growth of crystals across the surface of the mold. The frozen cell substrate solution can be removed from the mold and freeze dried to sublimate the crystals. In some examples, the cell substrate is seeded with cells by using a pressurized system to force a cell mixture through the cell substrate.

To illustrate, in some implementations, the disclosed method comprises injecting a cell substrate solution into a mold comprising a surface having a wettability gradient and cooling the surface of the mold. By cooling the mold's surface, the disclosed method can both freeze the cell substrate solution and form a temperature gradient within the mold that helps nucleate crystals. After removing the frozen cell substrate solution from the mold, the method includes freeze drying the frozen cell substrate solution to sublimate the nucleated crystals and form a cell substrate. Having formed the cell substrate, the method can further include seeding cells onto the cell substrate.

In some embodiments, the disclosed method comprises use of an apparatus to form a cell substrate for lobster muscle cells, scallop muscle cells, or other muscle cells. The disclosure describes an apparatus for forming a structured porous cell substrate. For example, the apparatus can comprise a metal surface having a wettability gradient, a plastic cover, and an inlet for cell substrate solution intake. In some cases, the plastic cover takes on a cylindrical or bi-cylindrical shape to mimic the shape of muscles from a lobster tail, a prawn tail, or other shellfish.

As mentioned, the disclosed method comprises injecting a cell substrate solution into a mold comprising a surface having a wettability gradient. To create such a wettability gradient, a coating is applied to the mold's surface, such as a coating applied to a metal plate that forms part of the mold. Upon application and treatment of the coating, the surface has relatively hydrophobic areas that transition into relatively hydrophilic areas. Generally, the wettability gradient on the surface directs a droplet's location. During freezing, the wettability gradient leads to a controlled nucleation of ice crystals across the surface.

In addition to leveraging such a wettability gradient, the disclosed method includes creating a temperature gradient by cooling the surface of the mold. By cooling a surface of the mold, the disclosed method likewise freezes the cell substrate solution that has been injected inside the mold. In some embodiments, the disclosed method creates a temperature gradient from the mold's surface up toward the top of the mold, where the surface is the coldest end and the top of the mold is the warmest end. The temperature gradient further controls or facilitates the nucleation of crystals within the mold.

After cooling a surface of the mold and the cell substrate solution within the mold, the disclosed method may comprise removing the frozen cell substrate solution from the mold. The frozen cell substrate solution comprises columns of nucleated crystals in an orientation consistent with the wettability and temperature gradients. As depicted and described by this disclosure, in one example, the columns have a perpendicular orientation relative to the frozen surface of the mold.

Having removed the frozen cell substrate solution, the disclosed method may include drying the frozen cell substrate solution. Drying dehydrates the frozen cell substrate solution by selectively removing ice crystals by sublimation, while leaving the cell substrate solution intact. Thus, the disclosed method removes the columnar crystals from the frozen cell substrate solution. In some cases, the resulting cell substrate has an aligned fibrous structure that can support growing cells. In some embodiments, the disclosed method dries the frozen cell substrate by freeze drying.

After freeze drying, the resulting cell substrate can accordingly be used to seed and grow cells. In some implementations, the disclosed method further comprises seeding the cell substrate. More specifically, in some embodiments, the disclosed method includes forming a viscous cell mixture. For example, the disclosed method may comprise suspending cells in an alginate solution. The increased viscosity of the cell mixture increases the likelihood that cells will adhere to the cell substrate during seeding. The cell mixture can then be pushed through or otherwise flowed or pressurized into the cell substrate to seed cells.

In one small scale example, the cell mixture is pushed through the cell substrate using a syringe. The cell substrate is placed on a sterile mesh within the barrel of a syringe. A cell mixture is created and added to the barrel of the syringe. In some embodiments, a cell mixture comprises a combination of cells with a cell substrate solution made of water, protein, and sodium alginate. The cell mixture is added to the barrel together with the cell substrate and the sterile mesh. The insertion of the syringe plunger seals the barrel of the syringe. When depressed, the plunger forces the cell mixture through the cell substrate. In a large scale example, a syringe-like system is used to create a pressure environment conducive to seeding cells within the substrate.

The disclosed method provides several benefits relative to existing methods for growing cell-based meats. In particular, the disclosed method utilizes a combination of a wettability gradient and a temperature gradient to control nucleation of crystals within a cell substrate. In some embodiments, the resulting cell substrate has an extensively aligned 3D fibrous structure similar to muscle tissue of shellfish. Furthermore, the cell substrate also functions as an extracellular matrix substitute that cues stem cells to differentiate and form a robust 3D tissue. The resulting texture of tissue grown in the cell substrate has improved texture more similar to harvested meat relative to cell-based-meat products grown using existing methods.

Unlike existing methods for growing cell-based meats, the disclosed method may form cell-based meat products similar in shape and texture to conventional shellfish. By creating a wettability gradient and a temperature gradient within a mold, the disclosed method forms parallel spikes of ice crystals within the mold. These spikes, when sublimated, form parallel honeycomb tubes of cell substrate. The parallel honeycomb structure closely resembles the tissue structure of various shellfish, including lobster tail and scallop meat. Furthermore, the disclosed method may utilize molds shaped to mimic different types of meat. For example, a mold may be shaped like a lobster tail, prawn tail, or an adductor muscle of a scallop.

As illustrated by the foregoing discussion, the present disclosure utilizes a variety of terms to describe features and advantages of the disclosed method. Additional detail is now provided regarding the meaning of such terms. For example, as used herein, the term "cell substrate solution" refers to a solution used to form a cell substrate. In particular, a cell substrate solution comprises a mixture having components or elements that can form a cell substrate. For example, a cell substrate solution can comprise a mixture of protein, water, and sodium alginate that solidifies into a cell substrate. Accordingly, a cell substrate can be edible. In some cases, the cell substrate constitutes a scaffold comprising a porous structure formed around nucleated crystals.

As used herein, the term "cell substrate" refers to a material on which cells attach or grow. In particular, a cell substrate includes a material to which cells adhere and upon which cells form a cellular tissue. A cell substrate can support or promote cell adhesion, cell differentiation, and/or growth of cells to form a cell mass, including a comestible meat product. For example, a cell substrate may comprise a three-dimensional porous matrix onto which cells may adhere and grow.

As used herein, the term "mold" refers to a hollow container used to give shape to a material. In particular, a mold includes a container having a shape of a desired meat product. For example, a mold may comprise a food-safe container in the shape of a chicken breast, lobster tail, scallop, lobster claw, or other portion of meat or part of an animal's body. The mold may additionally have a surface (e.g., an upper surface) exhibiting a shape that mimics the desired meat product and another surface (e.g., bottom surface) upon which cell substrate solution that may be flat or also exhibit the shape of a desired meat product. Also, a mold may include multiple surfaces or structures made of different materials (e.g., plastic, metal).

As used herein, the term "surface" refers to a part or layer of a body or other thing. In particular, a surface includes an inner part of a mold. A surface may comprise a metal or other conductive part of a mold. For example, a surface of a mold may comprise a metal cap having a wettability gradient on its face in one end of a columnar mold. By contrast, another surface may comprise plastic or other non-conductive part of the mold.

As used herein, the term "wettability gradient" refers to an increase or decrease in the magnitude of wettability observed in passing from one point to another. In particular, in a wettability gradient, wettability changes across different positions of a surface. More specifically, wettability is the measurement of the attraction of a liquid phase to a solid surface. For example, a surface can have a wettability gradient where the wettability continuously increases from one point of the surface to another point.

As used herein, the term "temperature gradient" refers to an increase or decrease in the magnitude of temperature in passing from one point to another. In particular, in a temperature gradient, the temperature changes across different positions in space. For example, a mold can have a temperature gradient where the temperature increases from one position within the mold to another position (e.g., coldest at the bottom of a mold to warmest at the top of the mold).

As used herein, the term "crystals" refers to pieces of homogenous solid substances. In particular, crystals can refer to pieces of solid ice. In some instances, crystals are formed by the process of nucleation. More specifically, nucleation refers to the process of forming a crystal from a solution, a liquid, or a vapor. For example, crystals may nucleate on a surface of a mold and grow during a cooling process.

As used herein, the term "cells" refers to cells of meat. In particular, cells may comprise different cell types, such as one or more of myoblasts, mesangioblasts, myofibroblasts, mesenchymal stem cells, hepatocytes, fibroblasts, pericytes, adipocytes, epithelial, chondrocytes, osteoblasts, osteoclasts, pluripotent cells, somatic stem cells, endothelial cells, or other similar cell types. Furthermore, cells may comprise different types of progenitor cells, including myogenic progenitors, adipogenic progenitors, mesenchymal progenitors, or other types of progenitor cells.

As used herein, the term "alginate solution" refers to a solution including alginate. In particular, an alginate solution comprises a liquid mixture in which sodium alginate is uniformly distributed within a solvent. For example, an alginate solution may comprise a measure of sodium alginate dissolved in water.

As used herein, the term "cell mixture" refers to a combination of substances and cells. In particular, a cell mixture comprises cells suspended in a solution for seeding a cell substrate. For example, a cell mixture can refer to cells suspended in an alginate solution.

Additional detail will now be provided regarding disclosed methods in relation to illustrative figures portraying example embodiments and implementations of the disclosed methods and apparatuses. FIG. 1 illustrates an overview of utilizing a temperature gradient and a wettability gradient to form a fibrous cell substrate in accordance with one or more embodiments. By way of overview, FIG. 1 illustrates a series of acts 100 including an act 102 of injecting a cell substrate solution into a mold, an act 104 of cooling the surface of the mold, an act 106 of removing the frozen cell substrate, an act 108 of drying the frozen cell substrate solution, and an act 110 of seeding cells onto the cell substrate.

Figure 2:
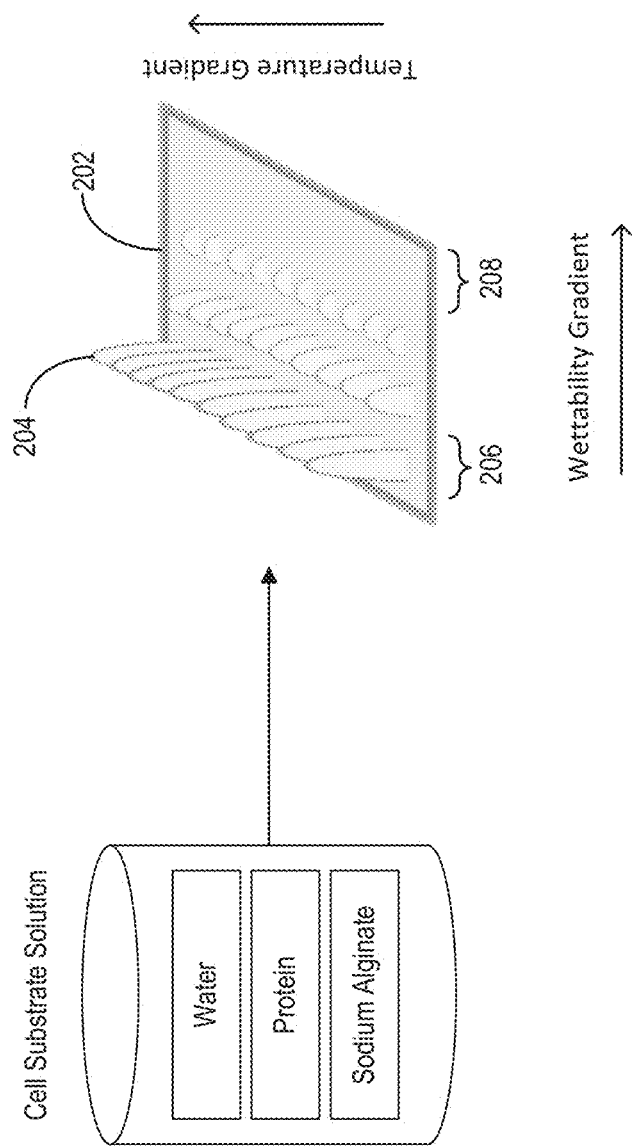
FIG. 2 illustrates forming organized ice crystals within a cell substrate solution utilizing a temperature gradient and a wettability gradient in accordance with one or more embodiments of the present disclosure.

As illustrated in FIG. 1, the series of acts 100 includes the act 102 of injecting a cell substrate solution into a mold. As illustrated, the disclosed method comprises injecting a cell substrate solution 116 into a mold 112. The mold 112 comprises a surface 114 having a wettability gradient. The wettability gradient on the surface 114 controls the formation of ice crystals that form with a lengthwise orientation that is perpendicular with a surface of the wettability gradient. The wettability gradient is on the face of the surface 114 that is in contact with the cell substrate solution 116. Generally, the cell substrate solution 116 contains water that freezes to form columnar structures within the cell substrate. FIG. 2 and the corresponding paragraphs further detail components of example cell substrate solutions.

Figure 3A:
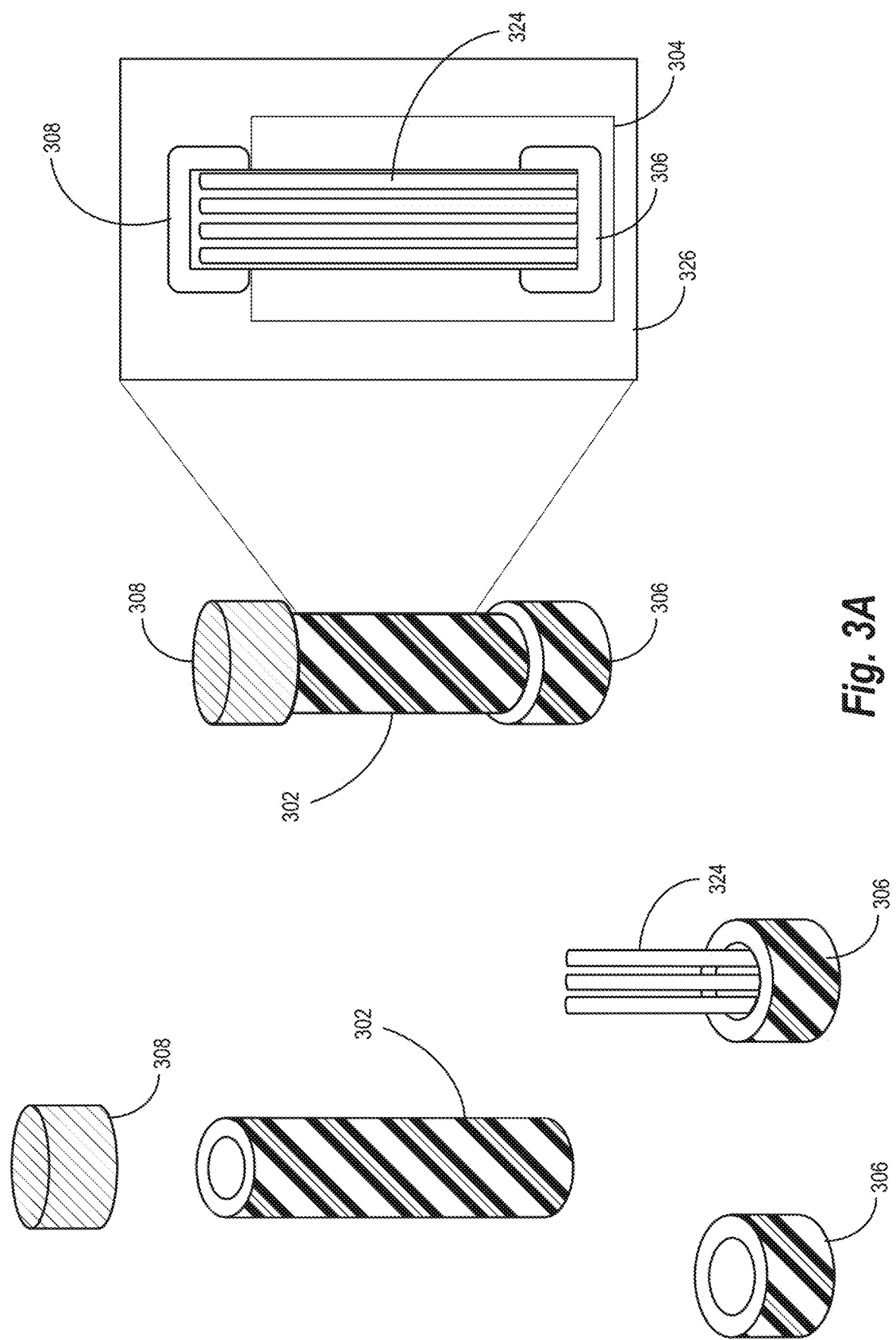
FIGS. 3A-3C illustrate a tubular mold and bi-semi-cylindrical mold in accordance with one or more embodiments of the present disclosure.
Figure 3B:
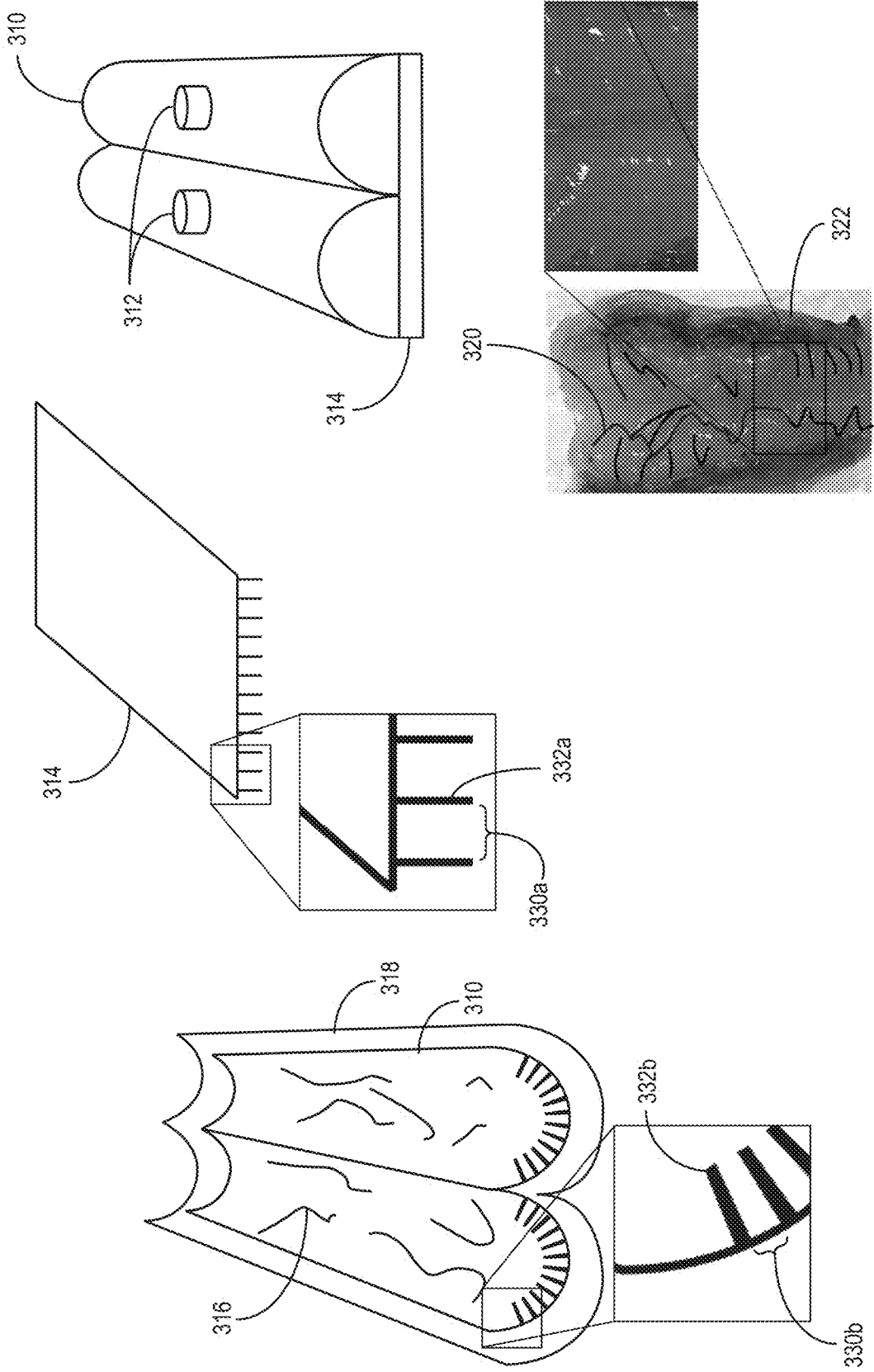
Figure 3C:
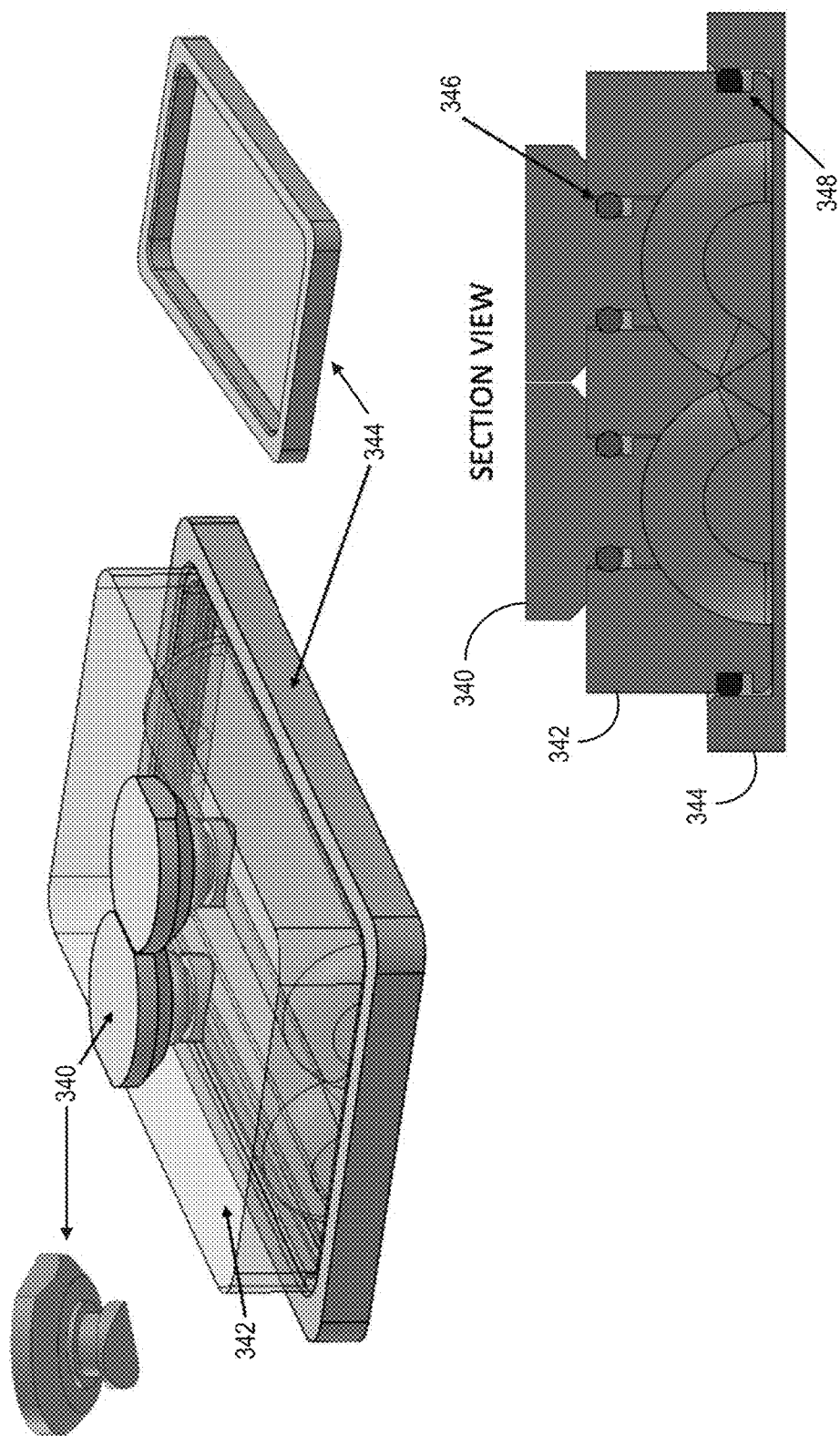

In some implementations, the surface 114 of the mold 112 comprises or constitutes a metal or a similar material having high heat conductivity. The remaining surfaces of the mold 112 may comprise plastic or other materials having low heat conductivity. FIGS. 3A-3C illustrate example molds in accordance with one or more embodiments.

FIG. 1 further illustrates the act 104 of cooling the surface of the mold. As illustrated in FIG. 1, the act 104 comprises cooling the surface 114 of the mold 112 to form a temperature gradient (indicated by ΔT) within the mold. In some cases, ice or other cooling agent is placed underneath the mold 112 to cool the mold 112 and freeze the cell substrate solution. A cooling agent is applied such that the surface 114 is the coldest point and an end 118 (or top surface) is the hottest point of the mold 112. By cooling the surface 114, the disclosed method begins nucleating ice crystals within the cell substrate solution 116. More specifically, the temperature gradient controls the growth of ice crystals because water from the cell substrate solution 116 starts to freeze at the coldest point, e.g. a point of nucleation, and continues to freeze toward the hottest point.

After cooling the surface 114 of the mold 112, the series of acts 100 illustrated in FIG. 1 further illustrates the act 106 of removing the frozen cell substrate. In particular, the act 106 comprises removing the frozen cell substrate solution 120 from the mold 112. In some embodiments, the combination of the wettability and temperature gradients in the mold 112 during cooling results in the frozen cell substrate solution 120 having columns or spikes of ice crystals oriented perpendicularly to the wettability gradient.

In some implementations, the acts 100 include an additional act of re-freezing the frozen cell substrate. The act of re-freezing ensures that all parts of the frozen cell substrate solution 120 remain frozen. In some cases, parts of the frozen cell substrate solution 120 may melt during the removal of the frozen cell substrate solution 120 from the mold 112. For example, the frozen cell substrate solution 120 may be frozen for a re-freezing period (e.g., 10-15 minutes) to further solidify the frozen cell substrate solution 120.

Figure 4:
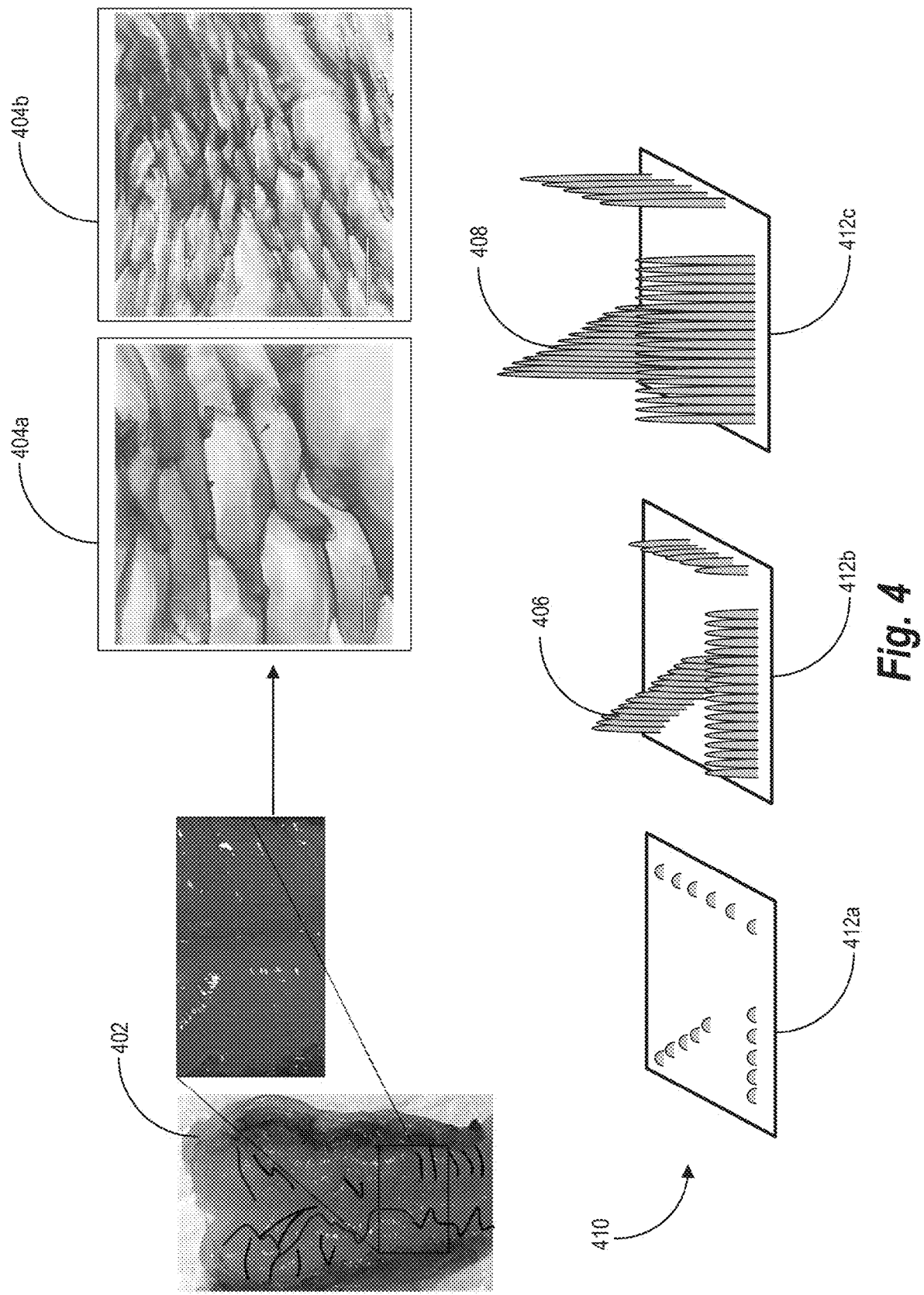
FIG. 4 illustrates porous aligned hollow fibers found in a cell substrate formed using wettability and temperature gradients in accordance with one or more embodiments of the present disclosure.

After removing the cell substrate from the mold, as further shown in FIG. 1, the series of acts 100 may further include the act 108 of drying the cell substrate solution. In particular, the act 108 comprises drying the frozen cell substrate solution 120 to sublimate nucleated crystals 122 and form a cell substrate 124. The act 108 can comprise freeze drying the frozen cell substrate solution 120 for a freeze-drying period (e.g., 48 hours). During the freeze-drying period, the nucleated crystals 122 sublime or vaporize. Because the nucleated crystals 122 formed columns, the sublimation of the nucleated crystals 122 leaves channels, pores, or tubes in the frozen cell substrate solution 120. The cell substrate 124 comprises a multitude of stacked planar layers capable of supporting layered tissue growth. FIG. 4 and the corresponding discussion describe characteristics of the resulting cell substrate.

Figure 5:
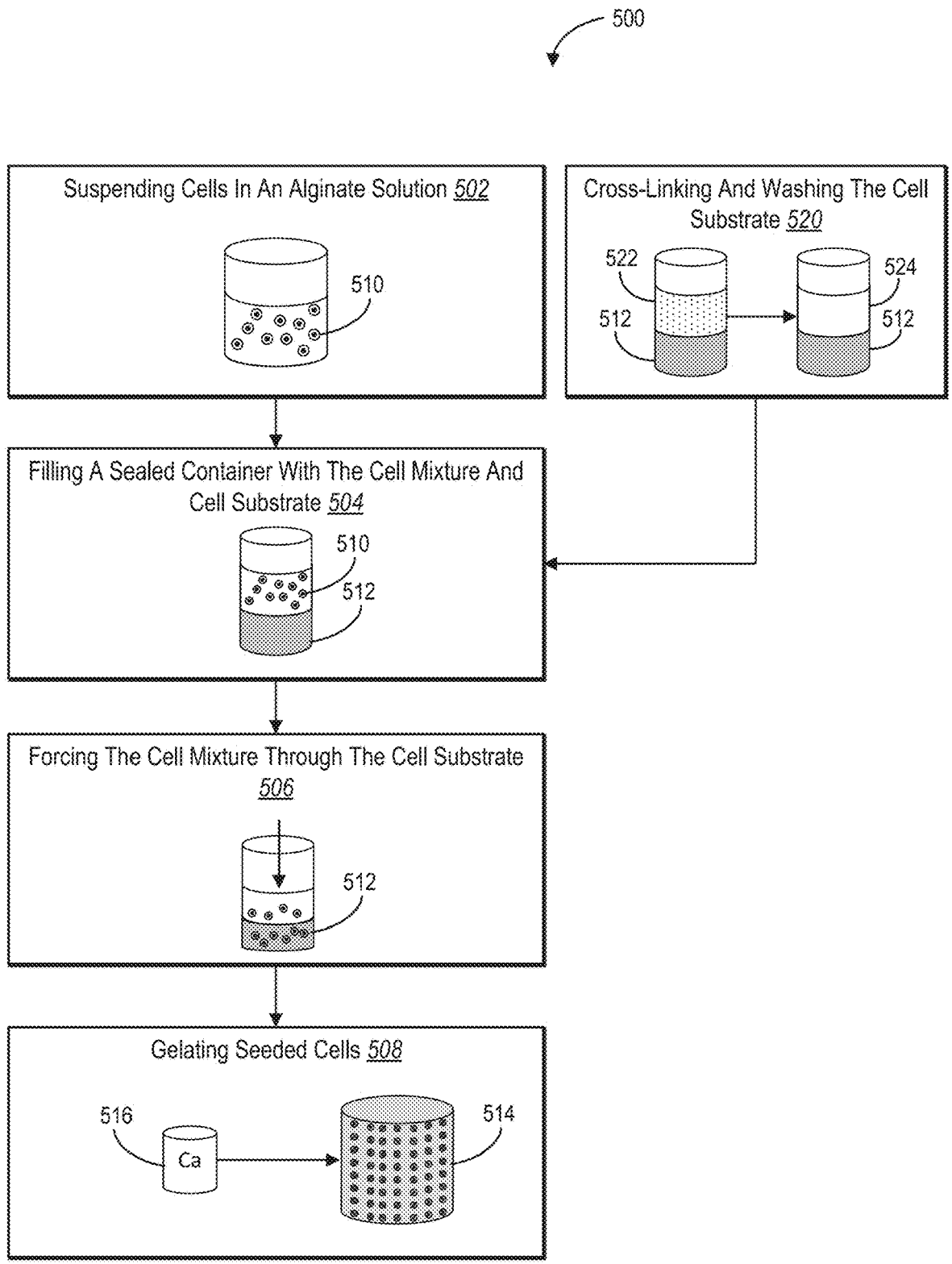
FIG. 5 illustrates an overview diagram of seeding cells through a cell substrate in accordance with one or more embodiments of the present disclosure.
Figure 6:
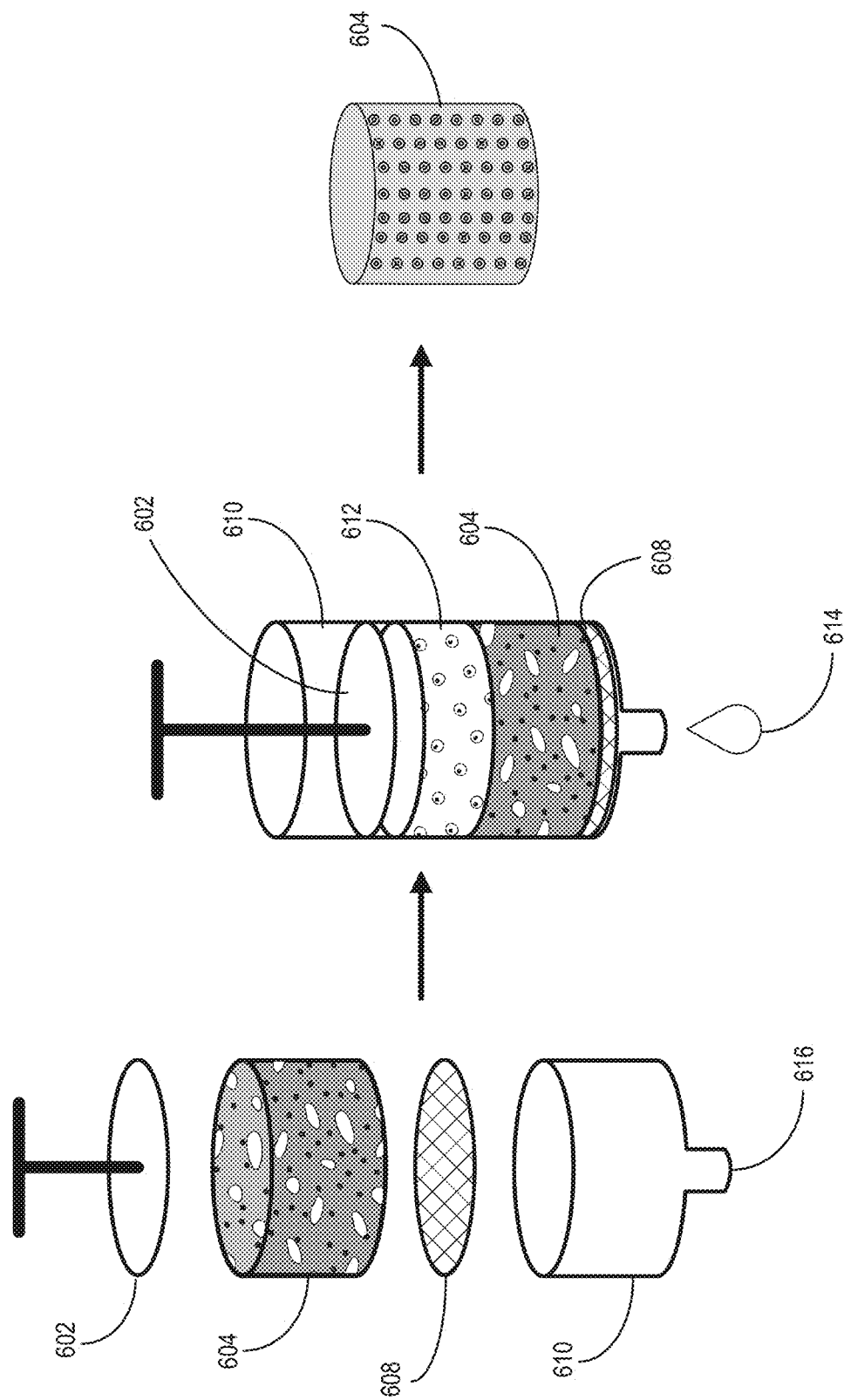
FIG. 6 illustrates an example sealed container for seeding a cell substrate in accordance with one or more embodiments of the present disclosure.

Having dried the cell substrate solution, as further shown in FIG. 1, the disclosed method further includes the act 110 of seeding cells onto the cell substrate. As illustrated, the disclosed method comprises seeding cells 126 onto the cell substrate 124. The disclosed method may include various techniques for seeding the cells 126 deep into the cell substrate 124. More specifically, the cells 126 coat and exterior surface of the substrate and also enter and land in the channels within the cell substrate 124. In some embodiments, the cells 126 are suspended in an alginate solution and pressed or otherwise forced through the cell substrate 124. Additionally, or alternatively, the disclosed method comprises suspending the cells 126 in a collagen solution or a gelatin solution. For example, the disclosed method may comprise suspending lobster cells in an alginate solution. The disclosed method may further comprise suspending different cells (e.g., chicken, cow, etc.) in solutions comprising collagen and/or gelatin. FIGS. 5-6 illustrate seeding cells onto the cell substrate in accordance with one or more embodiments.

As mentioned, the disclosed method comprises using a wettability gradient to form a layered cell substrate from a cell substrate solution. In accordance with one or more embodiments, FIG. 2 depicts an example cell substrate solution and a wettability gradient.

Figure 7A:
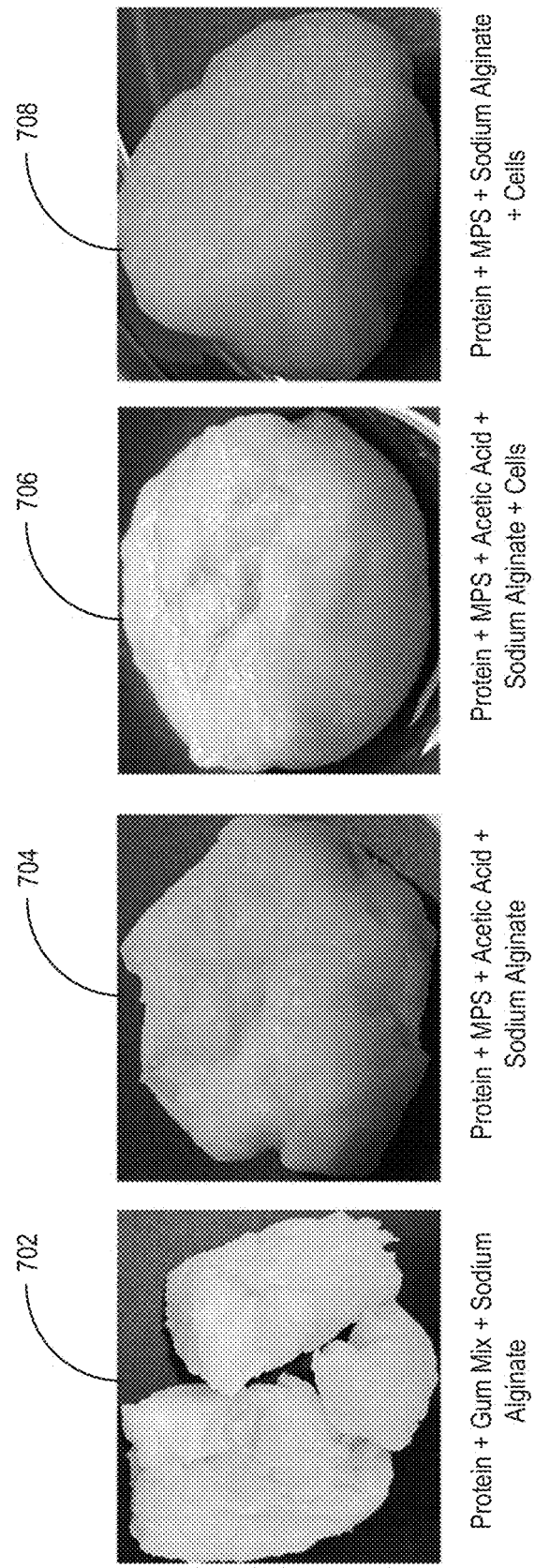
FIGS. 7A-7C illustrate a series of various cell substrates and lobster tissue in accordance with one or more embodiments of the present disclosure.
Figure 7B:
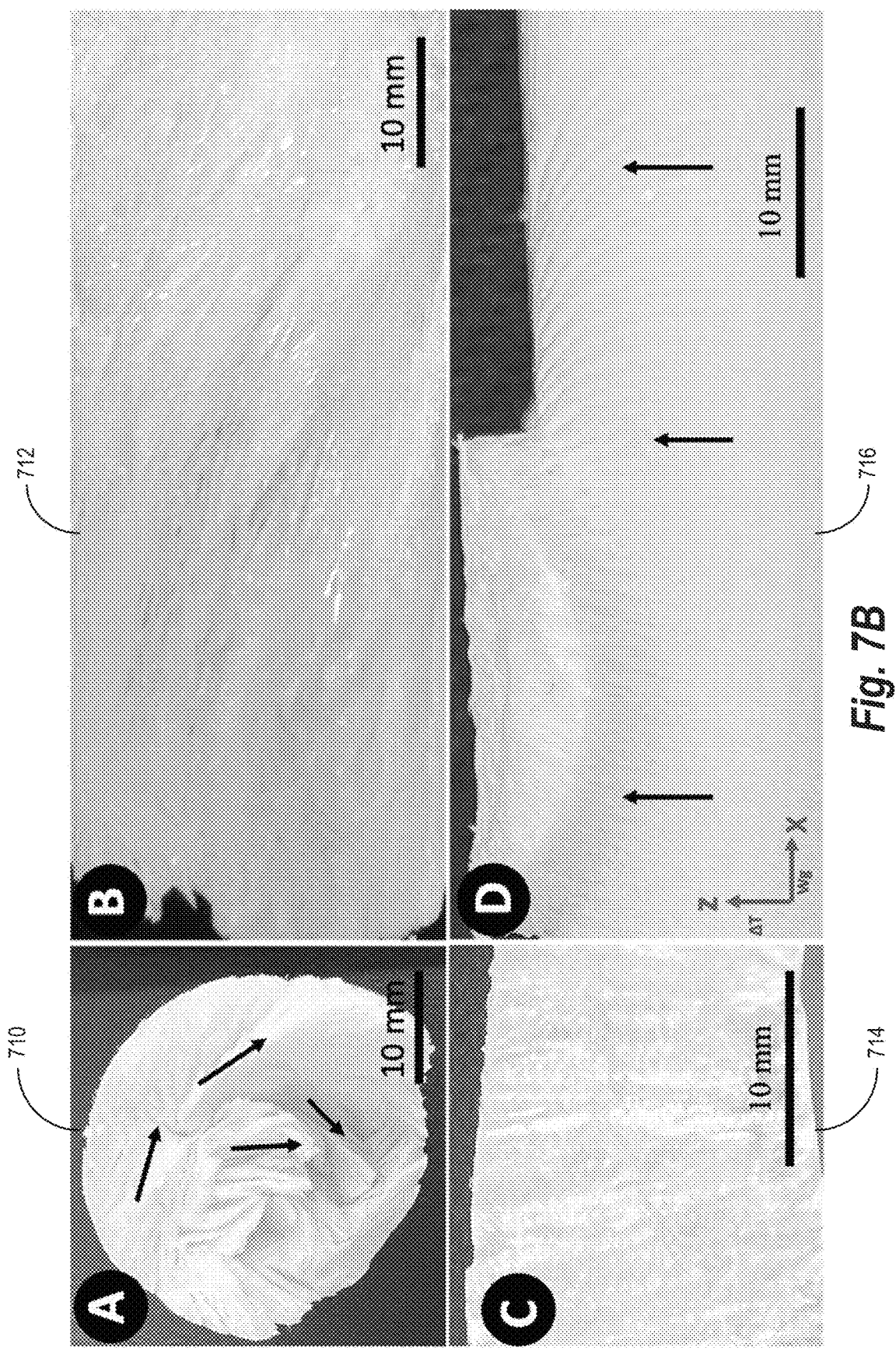
Figure 7C:
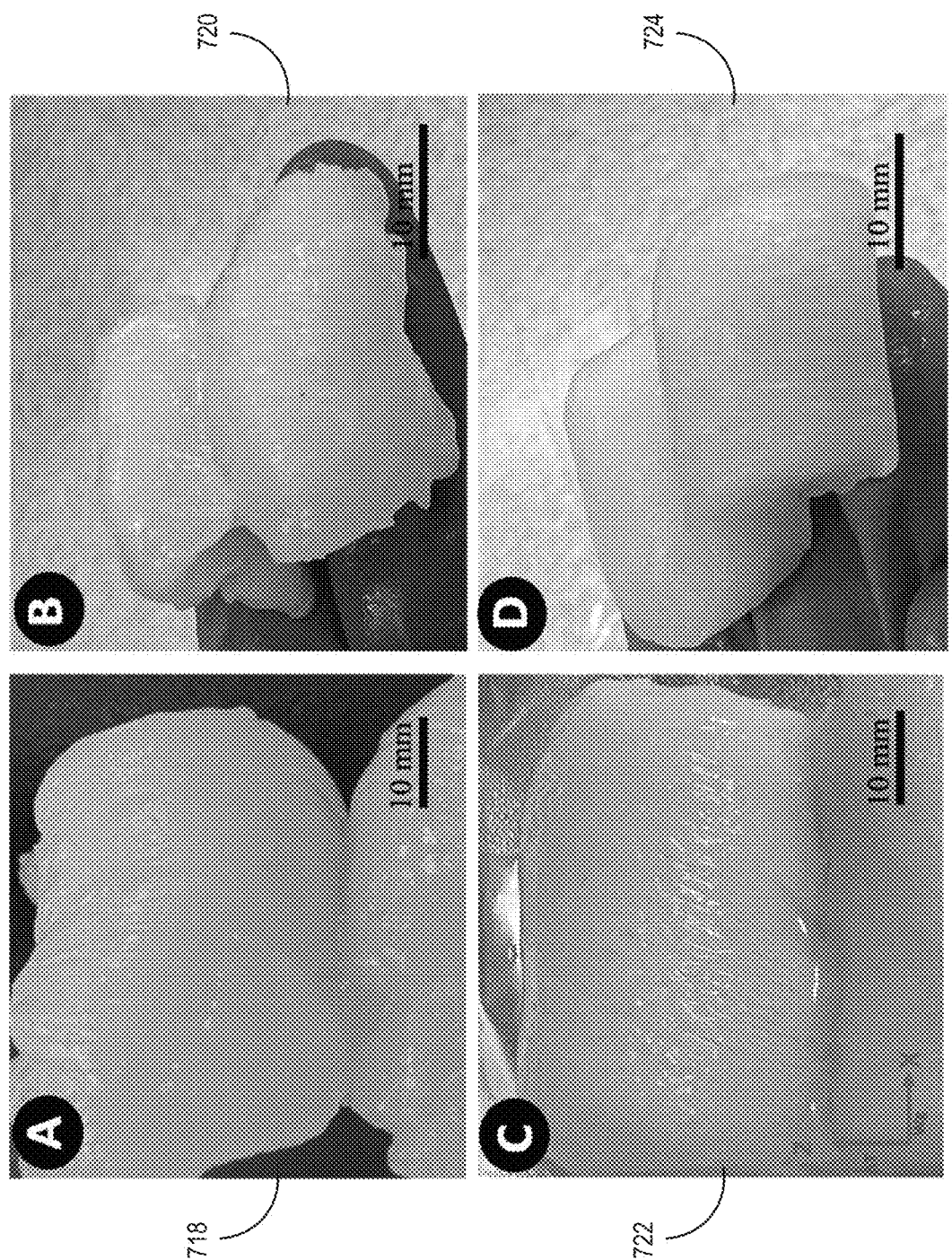

In particular, FIG. 2 illustrates example components of a cell substrate solution. In some examples, the cell substrate solution comprises at least three primary components-water, protein, and sodium alginate. Generally, the components of the cell substrate solution affect properties of the resulting cell substrate. Special ratios of protein, carbohydrate sources, cross-linker, and cross-linking methods correspond with different physical properties of the resulting cell substrate. FIGS. 7A-7C and the corresponding discussion further detail example protein sources and cross-linking methods utilized in cell substrate formation.

The various components of the cell substrate solution provide different benefits. The water forms ice crystals in the frozen cell substrate solution that form the channels and tubes in the final cell substrate. The protein generally comes together to form a relatively stable configuration. The sodium alginate can be used as a thickening or gelling agent in the cell substrate.

The cell substrate solution is prepared by adding sodium alginate to water until dissolved. Protein is then gradually added to the sodium alginate solution and mixed until homogenous. In one example, the disclosed method includes adding 100 mL Millipore water to a container with a stirrer (e.g., a magnetic bar). The stirrer is turned on (e.g., 200 RPM) and 1 g of sodium alginate is added to make a 1% sodium alginate solution. In other embodiments, a different concentration of sodium alginate (e.g., 2%, 20%, etc.) is used. The speed of the stirrer may gradually increase according to the viscosity of the sodium alginate solution.

Protein (e.g., whey protein, soy protein, other plant-based proteins, etc.) is gradually added to the solution, and the cell substrate solution is mixed until homogenous. The protein may be added to meet a protein concentration (e.g., 8%). In some implementations, the ratio of protein and sodium alginate concentrations are close to the ratio of protein and carbohydrate found in slaughtered meat. For instance, the concentrations of protein and sodium alginate can be adjusted to mimic the protein and carbohydrate concentrations found in lobster meat. The cell substrate solution can further be centrifuged at a speed (e.g., 3000 rpm) for a centrifugation period (e.g., 15, 20, 30, etc. minutes) to remove air bubbles from the cell substrate solution.

FIG. 2 further illustrates how the use of a temperature gradient and wettability gradient form parallel spikes of ice that, when sublimated, form parallel tubes of cell substrate that support the growth of cells seeded in the tubes. As illustrated in FIG. 2, a temperature gradient is created within a mold by cooling a surface 202 of the mold. In some implementations, the surface 202 is cooled by applying a cooling agent, such as dry ice, a cooling pack, or ice, to the surface 202 or by exposing the surface 202 to liquid nitrogen. Cooling the surface 202 cools one end of the mold to a greater extent than the opposite end of the mold. The relative position of the mold to the cooling agent and the surface 202, therefore, forms a temperature gradient across the mold.

The temperature gradient created by cooling the surface 202 nucleates crystals in the cell substrate solution within the mold. More specifically, nucleation occurs when water molecules in the cell substrate solution begin to gather into tiny clusters and arrange in a way that define the structure of the crystals. Because the surface 202 is the coldest point within the mold, water molecules begin to nucleate on the surface 202. The temperature gradient directs the growth of the crystals to be perpendicular to the surface 202. To illustrate, a crystal 204 is formed beginning with nucleation at the surface 202 and grows upward toward the warmest point in the mold.

In some embodiments, the rate of freezing affects the width of the ice crystal columns. For example, higher rates of heat loss correspond with thinner ice crystal columns. Lower rates of heat loss or freezing correspond with thicker ice crystal columns. Subsequently, cell substrates formed using higher rates of heat loss have larger pores, and substrates formed using lower rates of heat loss have smaller pores. More specifically, when the rate of heat loss is lower, the ice crystal columns have more time to form larger columns. The rate of heat loss can be controlled using the amount of surface area exposed to the cooling agent. For example, a mold with a smaller metal surface exposed to a cooling agent (e.g., dry ice) can result in lower rates of freezing. A mold with a larger metal surface exposed to the cooling agent can result in higher rates of freezing and, thus, cell substrates with larger pores. In another example, the rate of heat loss is controlled or slowed by adding insulating layers between the metal surface and the cooling agent.

While the temperature gradient facilitates the upward growth of crystals relative to the surface 202, the wettability gradient guides the alignment of the crystals. Generally, wettability is a measurement of liquids' ability of interaction with a solid surface. In other words, wettability of the surface 202 refers to its hydrophilic or hydrophobic nature. Points with higher wettability (e.g., where the hydrophilicity is relatively higher) increase the contact area of liquid droplets with the points relative to the solution's volume. Therefore, the rate of heat loss on a hydrophilic point is more than the heat loss at a hydrophobic point in the same material. Hence, ice crystals nucleate faster at hydrophilic areas than at hydrophobic areas.

As illustrated in FIG. 2, the surface 202 has a relatively higher wettability region 206 and a relatively lower wettability region 208. More specifically, more water molecules in the cell substrate solution interact with the surface 202 at the relatively higher wettability region 206 than at the relatively lower wettability region 208. Thus, when the surface 202 is frozen, crystals begin to nucleate at the relatively higher wettability region 206 before they begin to nucleate at the relatively lower wettability region 208.

As further illustrated in FIG. 2, in some embodiments, the wettability gradient facilitates the formation of layers of planar sheets. In particular, the ice crystals begin to form in rows based on the wettability gradient. Because ice crystals begin forming earlier at the relatively higher wettability region 206, they roughly form a first row of ice crystals. In some implementations, the ice crystals join together to support the formation of layered planes of substrate.

In some implementations, the disclosed method comprises preparing the wettability gradient on the surface 202. The disclosed method may use various techniques to create the wettability gradient on the surface 202. Generally, the disclosed method forms the wettability gradient by applying a coating material to the metal surface, treating the coated metal surface, and cleaning the metal surface.

To illustrate one such coating process, in some embodiments, the surface 202 comprises titanium, iron, copper, zinc, aluminum, tin, or another electrically conductive metal. The disclosed method comprises placing two cleaned metal plates in an electrolytic cell. The plates are designated as a working electrode and a counter electrode. The electrolyte comprises an ethanol solution of n-tetradecanoic acid 0.5M. The disclosed method comprises treating the system with a current (e.g., 5-volt DC) for a wettability treatment period (e.g., 3 hours) at room temperature. The working electrode is subsequently rinsed thoroughly with de-ionized water and ethanol. The working electrode is air dried and becomes the surface 202. The hierarchical micro- and nano-structures endow the surface 202 with excellent superhydrophobicity even for some corrosive liquids including salt, acidic, and basic solutions at all pH values.

While the previous paragraph describes one method for creating a wettability gradient on the surface 202 using a coating, the disclosed method may comprise other techniques for forming the wettability gradient. For instance, the disclosed method may immerse a metal plate in different solutions, such as an ethanol solution of n-tetradecanoic acid (0.01M), an aqueous silver nitrate solution ($1 \times 10^{-3}$M to $100 \times 10^{-3}$M) with or without a concentration of benzoic acid, an aqueous solution of $K_2S_2O_8$ (0.65M) and KOH (2.5M), or another solution. The plate may be immersed in the solution for an immersion period (e.g., 3-5 days, 1-1080 minutes, 10-30 minutes, etc.). After the immersion period, the metal plate is rinsed with deionized water and ethanol and air dried.

In some embodiments, the plate is further treated. For instance, plates immersed and soaked in an aqueous solution of $K_2S_2O_8$ and KOH may be further spin coated with poly (dimethylsiloxane) vinyl terminated (PDMSVT) and cured in a heater at a curing temperature (e.g., 120 C) for a curing period (e.g., 2 hours). The disclosed method includes these and/or other procedures for creating a wettability gradient on the surface 202.

As further illustrated in FIG. 2, the temperature gradient and the wettability gradient facilitate the formation of ice crystals having lengths parallel to the temperature gradient and perpendicular to the wettability gradient. While the water in the cell substrate solution freezes into the columns, the other components of the cell substrate solution support the formation of a scaffold or substrate having a layered-parallel sheet-like structure. More specifically, layers of cell substrate are formed along the wettability gradient along the length of the mold, thereby forming parallel sheets oriented perpendicular to the wettability gradient. This kind of layered structure closely resembles the tissue structure of some conventional meat. In some examples, the structure of the cell substrate mimics the structure found in shellfish, such as lobster meat, prawn meat, and scallop meat.

FIG. 2 illustrates crystal nucleation on a frozen surface having a wettability gradient. As mentioned, in some embodiments, the cooled surface comprises one end of a mold. FIGS. 3A-3C illustrate example molds in accordance with one or more embodiments. The molds depicted in FIGS. 3A-3C form cell substrates into a tubular shape and a lobster tail. As the following paragraphs describe, the molds comprise the surface at a coldest end and an opposite warmest end. While FIGS. 3A-3C illustrate example molds, additional mold shapes mimicking other types and shapes of meats (e.g., chicken breast, lobster claw, etc.) are possible.

FIG. 3A illustrates an example mold in accordance with one or more embodiments. Generally, FIG. 3A depicts a tube mold comprising a plastic tube 302, a plastic cap 306, and a metal cap 308. The plastic tube 302 includes a cylindrical compartment. As illustrated, the plastic tube 302 and the plastic cap 306 are made of non-conductive material to maintain the temperature gradient. By contrast, in some embodiments, the metal cap 308 is made of conductive material to create the temperature gradient within the mold. Due to a coating or other preparation, in some embodiments, the metal cap 308 exhibits a wettability gradient on the inside face. In at least one example, the tubular mold illustrated in FIG. 3A or a similarly shaped mold is used to form cell substrates for growing cell-based scallop meat.

As further illustrated in FIG. 3A, in some implementations, the mold comprises silicone extensions 324 for forming pores in the structured porous cell substrate. In some embodiments, the silicone extensions 324 are attached to the plastic cap 306. The pores in the cell substrate can be filled with cell culture media so that nutrients can penetrate the interior of the cell substrate. In some cases, cell culture media is limited by a media penetration depth (e.g., 2.5-3 mm) of the scaffold, so regularly spaced large pores (e.g., 1.5-4.5 mm) can ensure that cell culture media can penetrate the cell substrate and contact all cells. The silicone extensions 324 are spaced according to the media penetration depth. For instance, for a cell scaffold having a media penetration depth of 2.5-3 mm, the silicone extensions 324 are spaced 5-8 mm apart. The silicone extensions 324 form a 3D array oriented left to right, top to bottom, and front to back. The silicone extensions 324 may be attached to the plastic tube 302 or the metal cap 308. In some cases, the mold comprises rods other than silicone extensions, such as another type of plastic rods.

As indicated above, the metal cap 308 may be cooled using dry ice or another cooling agent to create a temperature gradient. Because of a temperature gradient formed by cooling the metal cap 308, the end of the metal cap 308 is the coolest point and the end of the plastic cap 306 is the warmest point. While FIG. 3A depicts the plastic tube 302 and the plastic cap 306 made of plastic, in some examples, the tube and the cap are also made of metal. The disclosed method may maintain the temperature gradient in such instances by utilizing an insulating material 304, such as foam.

FIG. 3A further depicts the insulating material 304 covering the plastic cap 306 and the plastic tube 302. The insulating material 304 may be used to insulate the plastic tube 302 and the plastic cap 306 to maintain the temperature gradient when the metal cap 308 (comprising a surface of the tube) is cooled by immersing the mold in liquid nitrogen.

The disclosed method may include preparing the mold for cooling. In some implementations, the disclosed method includes washing and drying the plastic tube 302, the plastic cap 306, and the metal cap 308. The disclosed method may further include applying a lubricant (e.g., petroleum jelly) to the threads of the plastic tube 302 where the metal cap 308 attaches for easy removal. The cell substrate solution may be poured into one of the ends of the plastic tube 302 or some other inlet for flowing the cell substrate solution into the mold.

In some implementations, the mold comprises a bi-semi-cylindrical mold. For instance, a bi-semi-cylindrical mold can be shaped like a lobster tail. FIG. 3B depicts a lobster tail mold in accordance with one or more embodiments. As used herein, the term "lobster tail mold" refers to a bi-semi-cylindrical mold. In particular, a bi-semi-cylindrical mold comprises a bi-cylindrical plastic cover and a flat surface. A lobster tail mold may be utilized to form a cell substrate having the shape of a bi-semi-cylindrical lobster tail. In some examples, a lobster tail mold or a bi-semi-cylindrical mold may be used to form cell substrates mimicking slaughtered meats having different shapes including shrimp, crawfish, langoustine, or other types of meat.

FIG. 3B illustrates a lobster tail mold comprising a bi-cylindrical plastic cover 310, inlets 312 for cell substrate solution intake, and a metal surface 314 having a wettability gradient. FIG. 3B further depicts insulating material 318 that may cover the bi-cylindrical plastic cover 310. As depicted, the bi-cylindrical plastic cover 310 comprises two semi-cylindrical compartments that mimic a shape of a lobster-tail meat.

As further shown in FIG. 3B, in some embodiments, the bi-cylindrical plastic cover 310 comprises grooves 316 that cause a cell substrate to have surface texture after formation. The grooves 316 and the shape of the mold depicted in FIG. 3B form a cell substrate similar in appearance to lobster meat 322. For instance, the grooves 316 form impressions in the cell substrate that mimic surface texture 320 found in the lobster meat 322.

The lobster tail mold illustrated in FIG. 3B also includes silicone extensions 332a-332b. Similar to the silicone extensions 324 depicted in FIG. 3A, the silicone extensions 332a-332b in FIG. 3B form large pores in the resulting cell substrate. The disclosed method may include the silicone extensions 332b attached to the bi-cylindrical plastic cover 310 and/or the silicone extensions 332a attached to the metal surface 314. In any case, in certain embodiments, the silicone extensions 332a-332b form a 3D array across the mold to create large pores that allow cell culture media to penetrate the cell substrate. As depicted, the silicone extensions 332a-332b are placed within spacing distances 330a-330b from each other. As mentioned previously, the spacing distances 330a-330b are determined based on a media penetration depth. For instance, for cell substrates having a media penetration depth of 2.5-3 mm, the silicone extensions 332a-332b can be spaced 5-8 mm apart. In addition to facilitating media circulation within the cell scaffold, the silicone extensions 332a-332b also create pore-like vessels similar to vessels found within the lobster meat 322.

To prepare the lobster tail mold for freezing, in some embodiments, the disclosed method includes washing and drying the bi-cylindrical plastic cover 310 and the metal surface 314. The bi-cylindrical plastic cover 310 and the metal surface 314 are assembled. As illustrated, the inlets 312 comprise caps that may be opened for filling and sealed during freezing. In some cases, the disclosed method comprises transferring the cell substrate solution into the bi-cylindrical plastic cover 310 through the inlets 312. The insulating material 318 is placed on the mold to cover the bi-cylindrical plastic cover 310.

As mentioned, different rates of freezing can result in different fiber structure widths in the produced cell substrate. For example, if a cooling agent is applied to the entire area of the metal surface 314, the rate of freezing the cell substrate solution could be significantly higher than if a cooling agent is applied to the smaller area of the metal cap 308 depicted in FIG. 3A. Thus, in some implementations, the pore or fiber width in cell substrates formed in the lobster tail mold is smaller than the fiber size in cell substrates formed in the tube mold illustrated in FIG. 3A.

FIG. 3C depicts a bi-semi-cylindrical mold made of different materials. In particular, FIG. 3C depicts a lobster tail mold comprising different material substances. The lobster tail mold portrayed in FIG. 3C comprises a bi-cylindrical cover 342, plugs 340, a stainless-steel base 344, plug seals 346, and base seals 348. As mentioned previously, the disclosed method may utilize a plastic bi-cylindrical cover. In some implementations, the plastic bi-cylindrical cover and the plugs are made of Teflon. In other implementations, the disclosed method may utilize a bi-cylindrical cover and/or plugs made of a different type of synthetic polymer.

FIG. 3C further depicts the plugs 340. The plugs 340 stop inlets to prevent the cell substrate solution from escaping the lobster tail mold during the freezing process. The plug seals 346 may be adhered or otherwise attached to the plugs 340. The plug seals 346 prevent leaks and ensure a tight and secure fit between the plugs 340 and the inlets. The plug seals 346 prevent cell substrate solution leakage.

As further illustrated in FIG. 3, the lobster tail mold may comprise the stainless steel base 344. The stainless steel base performs the function of the metal surface. In some examples, the stainless steel base 344 contains a wettability gradient. The base seals 348 prevent leakage between the stainless steel base 344 and the bi-cylindrical cover 342.

In some examples, the disclosed method comprises placing the bi-cylindrical cover 342 on the stainless steel base 344. The bi-cylindrical cover 342 can be tightened on the stainless steel base 344 to ensure a seal. Cell substrate solution is added to the bi-cylindrical cover 342 through one or more of the inlets, and the plugs 340 are secured in the inlets prior to freezing.

The lobster tail mold illustrated in FIG. 3C can be modified to increase the volume of cell substrate. For example, the lobster tail mold can be enlarged to create a larger cell substrate. In some embodiments, multiple lobster tail molds can be frozen simultaneously. A plurality lobster tail molds may be placed in certain configurations to maximize the number of cell substrates. For example, a plurality of lobster tail molds may be arranged in a configuration in which the ends of the plurality of lobster tail molds are centered at a locus. In another example, the lobster tail molds are stacked on top of each other.

The molds depicted in FIGS. 3A-3C are filled with cell substrate solution and cooled. The cell-substrate solution may be cooled by cooling the metal surface 314, the metal cap 308, and the stainless steel base 344. In some embodiments, the stainless steel base 344, the metal surface 314 and the metal cap 308 are put in contact with dry ice. The temperature of the metal surface 314, the stainless steel base 344, and the metal cap 308 when in contact with dry ice may be around −70 C, while the opposite end (e.g., the plastic cap 306 and the top of the bi-cylindrical plastic cover 310) remain at room temperature because of the insulating material.

In some cases, the disclosed method comprises freezing the cell substrate solution within the mold for a freezing period. Generally, the freezing period equals a time required to completely freeze the cell substrate solution. For example, the freezing period can equal 24 hours, 48 hours, or another period. Upon completion of the freezing period, the frozen cell substrate solution is removed from the mold. For the mold depicted in FIG. 3A, the frozen cell substrate solution can be removed by removing the metal cap 308 or the plastic cap 306. For the bi-cylindrical plastic cover 310 depicted in FIG. 3B, the frozen cell substrate solution is removed by taking apart the metal surface 314 and the bi-cylindrical plastic cover 310 to expose the frozen cell substrate solution. Similarly, for the lobster tail mold depicted in FIG. 3C, the frozen cell substrate solution is removed by taking apart the stainless steel base 344 and the bi-cylindrical cover 342.

As mentioned previously, the frozen cell substrate solution can be freeze dried to sublimate the nucleated crystals. In some embodiments, the frozen cell substrate solution is freeze dried for a freeze-drying period. For example, the frozen cell substrate solution is freeze dried for 48 hours. During freeze drying, the ice crystal columns sublimate and leave channels or tubes in an ordered matrix. For instance, in some implementations, the resulting cell substrate has parallel-honeycomb tubes of substrate with a diameter of 200-500 μm that support the growth of cells seeded in the tubes. In some examples, the resulting cell substrate is structured having parallel honeycomb tubes of substrate with diameters less than 200 μm or more than 500 μm.

The molds depicted in FIGS. 3A-3C can be modified to form cell substrates mimicking various types of meat. For example, the tubular mold depicted in FIG. 3A can be used to form cell substrates mimicking scallop meat. The tubular mold depicted in FIG. 3A may be narrowed and elongated to form cell substrates mimicking crab leg meat. Similarly, the bi-semi-cylindrical molds depicted in FIGS. 3B-3C can be modified to form cell substrates mimicking other types of meat in addition to lobster tail meat. For example, the bi-semi-cylindrical molds depicted in FIGS. 3B-3C can be scaled down to form cell substrates mimicking shrimp or langoustine tails.

FIG. 4 illustrates an example cell substrate having a fibrous structure similar to structure found in conventional shellfish meat in accordance with one or more embodiments. FIG. 4 illustrates a comparison between lobster meat 402 and cross-section images 404a and 404b of a cell substrate. FIG. 4 also depicts a series 410 of surfaces 412a, 412b, and 412c. The cross-section images 404a and 404b demonstrate the pores resulting from crystals 406 and crystals 408 that formed on the surfaces 412a-412c during freezing.

As illustrated in FIG. 4, the lobster meat 402 has parallel columns of muscle tissue. The disclosed method forms cell substrates with similarly structured parallel sheets of tubes. The cross-section images 404a and 404b are optical images of a cross-sectioned cell substrate at different magnifications. The cross-section images 404a and 404b depict parallel honeycomb tubes of substrate that support the growth of cells. The cell substrate has honeycomb porous aligned hollow fibers that increase mechanical strength of the cell substrate. More particularly, the layered structure seen in the cross-section images 404a and 404b recapitulates (or resembles) extracellular matrix found in epimysium, perimysium, and endomysium in the lobster meat 402. This structure improves myogenic differentiation and the mechanical strength of engineered tissue.

The honeycomb tubes are the result of the formation of ice crystals perpendicular with a wettability gradient as illustrated by the series 410 in FIG. 4. In particular, ice templating and controlling nucleation of ice crystals by wettability and temperature gradients results in the construction of the honeycomb fibrous substrate. Generally, the series 410 depicts the formation of crystals at different times within the freezing process. For instance, FIG. 4 depicts the surface 412a supporting crystals beginning to nucleate at a first time, the surface 412b supporting crystals beginning to grow at a second time, and the surface 412c supporting fully-grown crystals at a third time.

FIGS. 1-4 and the corresponding text describe forming a cell substrate comprising a structured porous matrix in accordance with one or more embodiments. In some embodiments, the disclosed method further comprises seeding the cell substrate. FIGS. 5-6 illustrate seeding the cell substrate with cells in accordance with one or more embodiments. More specifically, FIG. 5 depicts an overview of seeding a cell substrate. In particular, FIG. 5 illustrates a series of acts 500 including an act 502 of suspending cells in an alginate solution, an act 504 of filling a sealed container with the cell mixture and cell substrate, an act 506 of forcing the cell mixture through the cell substrate, and an act 508 of cross-linking seeded cells.

As illustrated in FIG. 5, the series of acts 500 includes the act 502 of suspending cells in an alginate solution. In particular, the act 502 comprises suspending cells in an alginate solution to form a cell mixture 510. In some embodiments, the cells are suspending in a sodium alginate solution that makes the cell mixture 510 more viscous and increases the chance of the cells sticking to the cell substrate rather than just passing through the pores or the layered planar sheets of the cell substrate.

The series of acts 500 illustrated in FIG. 5 further includes an act 520 of cross-linking and washing the cell substrate. More specifically, a cell substrate 512 is cross linked and washed in preparation for seeding. In some implementations, the cell substrate 512 is cross linked using a cross-linking solution 522. While the freeze-drying procedure formed an aligned fibrous structure and porosity in the cell substrate 512, the cell substrate 512 may eventually dissolve and gradually lose its structure. By cross-linking the cell substrate 512, the disclosed method forms covalent bonds between molecules and chains of polymers within the cell substrate 512 to maintain its structure.

In some implementations, the cross-linking solution 522 is added to the cell substrate 512 within a cross-linking period. Generally, the cross-linking period comprises a time between when the cell substrate 512 has been frozen and when the cross-linking solution 522 is added to the cell substrate 512. To illustrate, if calcium concentrations (e.g., $CaCl_2$) are relatively low (e.g., 5 g-10 g salt/L) in the cell substrate 512, then the cell substrate 512 may dissolve during or soon after drying. Thus, the cross-linking solution 522 is added within a cross-linking period (e.g., 1 minute) to keep the cell substrate 512 intact and initiate cross-linking.

In some cases, cross-linking the cell substrate 512 comprises immersing the cell substrate 512 in the cross-linking solution 522 for a cross-linking period (e.g., 45 minutes). Additionally, in some implementations, the cell substrate 512 is placed in an oven at a cross-linking temperature (e.g., 60 C) for a heated period (e.g., 15, 20, 25 minutes, etc.) for further cross-linking. The following paragraphs describe preparing the cell substrate 512 for cross linking and preparing the cross-linking solution 522.

In some embodiments, the act 520 includes preparing the cell substrate 512 for cross linking. Preparing the cell substrate 512 may comprise drying and heating the cell substrate 512. In one example, the cell substrate 512 is sealed in an autoclave bag and placed in an oven at 60 C for a heating period (e.g., 20 min).

The act 520 illustrated in FIG. 5 further comprises preparing the cross-linking solution 522. In one example, the disclosed method comprises preparing the cross-linking solution 522 by heating water and adding calcium gluconate at a determined concentration (e.g., 8% weight by volume). In another example, the disclosed method comprises preparing the cross-linking solution 522 by adding calcium chloride in the water at a determined concentration (e.g., 3% weight by volume). The disclosed method includes gradually adding the calcium gluconate and/or the calcium chloride to dissolve it in the water. The cross-linking solution 522 is cooled to room temperature before being added to the cell substrate 512.

Furthermore, as part of the act 520 illustrated in FIG. 5, the cell substrate 512 is washed with one or more washing solutions 524 in preparation for seeding. The washing solutions 524 can include water, an ethanol solution, and/or other buffer solutions. For example, washing the cell substrate 512 with water comprises removing cross-linking solution from the cell substrate 512 and adding water to a container holding the cell substrate 512. The cell substrate 512 and the water can be agitated, for instance, using a shaker, to wash the cell substrate 512 for a washing period (e.g., 15 minutes). The water washing process may be repeated several times (e.g., 3 times, 5 times, etc.).

The act of washing the cell substrate may additionally or alternatively include washing the cell substrate 512 using an ethanol solution. The ethanol wash is performed in an aseptic environment. The cell substrate 512 is washed using an ethanol solution (e.g., 70% ethanol) by removing the water from the cell substrate 512 and transferring the cell substrate 512 to a sterile container. The disclosed method includes adding the ethanol solution to the sterile container and sealing the container. The sterile container is agitated for an ethanol wash period (e.g., 1 hour, 5 hours, overnight, etc.). The ethanol wash may be repeated several times with varying ethanol wash periods.

Furthermore, in some embodiments, the act of washing the cell substrate further includes washing with other buffers. For example, the disclosed method can comprise washing the cell substrate 512 using LudgerSep (LS) and 4-(2-hydroxyethyl)-1-piperazineethanesulfonic acid (HEPES). For instance, the ethanol solution is removed from the cell substrate 512 and LS+HEPES is added to the cell substrate 512 and agitated for an LS+HEPES wash period (e.g., 1 hour, 5 hours, overnight, etc.). The LS+HEPES wash may be repeated several times with varying LS+HEPES wash periods. In some implementations, the cell substrate 512 is stored in a LS+HEPES solution in preparation for seeding.

As further illustrated in FIG. 5, the series of acts 500 includes the act 504 of filling a sealed container with the cell mixture and cell substrate. As illustrated, the disclosed method fills a container with the cell mixture 510 and a cross-linked and washed embodiment of the cell substrate 512. In some implementations, the sealed container can be pressurized to force cells within the cell mixture 510 through the cell substrate 512. For example, the sealed container can comprise a syringe, vacuum, or other type of sealed container.

The series of acts 500 illustrated in FIG. 5 also includes the act 506 of forcing the cell mixture through the cell substrate. In particular, the act 506 comprises forcing the cell mixture through the cell substrate 512 to seed cells throughout the cell substrate. In some embodiments, the sealed container applies pressure to seed the cell mixture 510 in the cell substrate 512. This mechanically assisted seeding leads to robust cellular integration throughout the entire cell substrate within a seeding time period. The seeding time period can be 5 seconds, 1 minute, 35 minutes, 1 hour, 2 hours, etc.

By using mechanical pressure, integration of cells throughout the cell substrate 512 occurs relatively quickly (within 35 minutes) compared to days or weeks required by existing unassisted methods. To illustrate, many existing methods take a long time for cells to seed because cells are allowed to proliferate and migrate into the substrate unassisted. The disclosed method includes forcing the cell mixture throughout the cell substrate. In one or more embodiments, the cell substrate 512 is placed in a syringe and cells are pushed through the cell substrate 512. As further described below, FIG. 6 depicts an example sealed container in accordance with one or more embodiments. In another example, the act 506 is performed by vacuum sealing the cell mixture 510 and the cell substrate 512 in the sealed container.

As further illustrated in FIG. 5, the series of acts 500 includes the act 508 of gelating seeded cells. Generally, the act 508 of gelating the seeded cells comprises forming a hydrogel to fix the cells in place in the cell substrate 512. In some cases, the act 508 of gelating the seeded cells is a finishing step. Gelating the seeded cells comprises a culmination of the steps of (i) producing the cell substrate 512 with desirable properties (e.g., organoleptic, nutritional, compatible with food formulation, etc.), (ii) culturing enough cells in a culture system, such as a bioreactor, and (iii) introducing the cells into the cell substrate 512 using the described pressure-assisted method.

In some examples, the act 508 comprises utilizing a calcium solution 516 to form a hydrogel that fixes cells in place. More specifically, calcium chloride can cross-link with sodium alginate to form a hydrogel. In some implementations, the calcium solution 516 is added to the seeded cell substrate 514 after cells have been seeded. The calcium solution 516 combines with the sodium alginate in the cell mixture 510 to gelate the seeded cells. In another example, the calcium solution 516 is added to the cell mixture 510 in preparation for seeding. By adding the calcium solution 516 to the cell mixture 510, the disclosed method increases the viscosity of the cell mixture 510 and also stimulates gelation after the cells have been seeded in the cell substrate 512.

Additionally, or alternatively, the act 508 comprises using temperature to gelate seeded cells. To illustrate, instead of adding the calcium solution 516, the disclosed method includes adding collagen that, when heated to a gelation temperature, forms a hydrogel and fixes the cells within the seeded cell substrate 514.

As mentioned, the disclosed method can comprise seeding lobster cells in a cell substrate. The following paragraphs describe a method for seeding a lobster tail cell substrate in accordance with one or more embodiments. Generally, lobster saline and media have high concentrations of calcium chloride ($CaCl_2$) that can cross-link the alginate solution. Lobster cells are extracted from lobster hematopoietic tissue and resuspended in an alginate solution. In some implementations, the sodium alginate viscosity is less than a sodium alginate threshold to prevent filling the pores in the cell scaffold. To illustrate, the sodium alginate viscosity can be less than 0.4% to prevent filling pores less than 500 micrometers across. The number of extracted lobster cells can equal $1.5 \times 10^7$ cells/cm$^3$ of cell substrate. This volume of lobster cells is resuspended in 5 mL (per 1 cm$^3$ of cell substrate) of the alginate solution.

In some embodiments, the disclosed method includes creating an alginate solution by obtaining lobster media with a threshold level of calcium chloride and adding sodium alginate to the lobster media. More specifically, the lobster media may have a concentration of calcium chloride below a threshold saline concentration (e.g., 20 g salt/L or 25 g salt/L). While calcium chloride can cross-link and gelate with sodium alginate, high concentrations of calcium chloride may be toxic to cells and decrease the viability of cells. In some implementations, some calcium chloride is left in the lobster media to cross-link the sodium alginate and make the cell media more gel-like for seeding.

In the lobster cell seeding example, the cell media comprising the lobster cells suspended in lobster media with sodium alginate is forced through the cell substrate. After seeding the lobster cells in the cell substrate, the cells are fixed in the cell substrate 512 by gelation. More specifically, in certain cases, the cell substrate is incubated in a plate at an incubation temperature (e.g., 16 C) for an incubation period (e.g., 20 minutes). The plate is filled with a lobster saline solution containing a higher concentration of $CaCl_2$ for a gelating period (e.g., 3 hours) in the incubator. The $CaCl_2$ in the lobster saline solution cross links the sodium alginate and makes a hydrogel in the cell substrate to gelate the seeded cells in place. The lobster saline solution is also high in salt. In contrast to typical saline solution that has a concentration of 5 g salt/L, lobster saline is typically 30 g salt/L.

In addition or in the alternative to lobster meat, the disclosed method may also be used to seed chicken or bovine cells in the cell substrate 512. Bovine or chicken cells may be suspended in an alginate solution that contains collagen. As mentioned, calcium chloride cross-links the alginate solution to form a hydrogel; however, higher calcium chloride concentrations kill chicken cells. Accordingly, collagen may be used in addition or in the alternative to calcium chloride in the alginate solution. The cell mixture comprising chicken/bovine cells and the alginate solution with collagen is forced through the cell substrate 512.

Unlike lobster cells that cannot tolerate incubation temperatures far above 18 C, chicken/bovine cells may be incubated at higher temperatures required for collagen gelation. The seeded cell substrate 514 is incubated at a collagen gelation temperature (e.g., 37-39 C) for a collagen gelation period (e.g., 15 minutes) to induce the gelation of collagen to create a hydrogel within the cell substrate. The chicken/bovine cells become trapped in the hydrogel. The seeded cell substrate 514 can be transferred to a perfusion bioreactor in the appropriate media.

One or more acts in the series of acts 500 may take place in environments of varying sterility. Generally, if the cells are not cultured after seeding in the cell substrate 512, then the seeding process may occur in a food grade clean environment that is open to ambient air rather than a sterile environment. Reducing the process requirement from sterile to clean dramatically reduces the cost of the equipment and processing time for seeding the cell substrate 512. Depending on whether the seeded cells will be further cultivated or not, the seeded cell substrate 514 may then proceed to downstream food formulations, or for a bioreactor for additional culture.

In some implementations, the disclosed method comprises seeding cells of different cell types. In particular, cells of different types (e.g., myocytes, adipocytes, fibroblasts, etc.) are combined and suspended in the alginate solution. The combined cells can be seeded in the cell substrate. Furthermore, in some implementations, the different cell types may be layered. For example, the disclosed method can comprise using a layered cell substrate having various pore sizes. To illustrate, the disclosed method can include layering a first cell substrate having a pores of a first size and a second cell substrate having pores of a second size.

Different cell types are captured in different pore sizes. For example, fibroblasts are trapped in larger pores and other cell types are trapped in smaller pores. To facilitate proper layering, the different cell types may be layered in the cell mixture. For instance, smaller cells are layered on the bottom while larger cells are layered on top. Because of the viscosity of the cell mixture and the cell size, the layers generally will not mix or will mix to a limited degree. In another approach, the disclosed method seeds cells of a first type, seeds cells of a second type, and then gelates the cells of the first type and the second type.

Existing methods used to organize cell scaffolds into specific structures are typically slow and not scalable. For example, 3D printing and bioprinting methods typically form cell scaffolds layer by layer and cannot be practically scaled. Furthermore, these existing systems are typically limited to thin sheets and require significant time for structures to form. However, the disclosed method allows tissue structure to be added to arbitrary volumes of substrates in brief amounts of time. For example, supportive fibroblasts can be alternated with myoblasts, and vascular progenitor cells at set depths of the tissue to generate a vascular network. In another example, fat cells can be dispersed at intervals during the seeding process to produce a desirable marbling pattern.

As mentioned, as part of seeding the cell substrate, the disclosed method includes forcing a cell mixture through the cell substrate. FIG. 6 illustrates an example procedure for seeding the cell substrate in accordance with one or more embodiments. 3D cell substrates often present seeding challenges for existing methods. As cells are flowed across cell substrates, cells often seed the top layers of the scaffold, block pores, and prevent deeper migration or penetration of other cells into the deeper layers of the scaffold. FIG. 6 illustrates an example method by which cells are forced into deep layers of a cell substrate using a pressure-based system. More specifically, the example sealed container can be used to press a cell mixture through a cell substrate using mechanical pressure and/or pulling the cell mixture through the cell substrate using vacuum pressure.

In particular, as shown in FIG. 6, the disclosed method includes placing a cell substrate 604 on a sterile mesh 608 in a barrel 610 of a container. A cell mixture 612 is also added to the barrel 610 before inserting a plunger 602. In some examples, the insertion of the plunger 602 seals the barrel 610 of the container. In some examples, the container has an outlet 616 for outflow. The outlet 616 has a significantly smaller diameter than the barrel 610 so that application of pressure to the plunger 602 pressurizes the system inside the barrel 610.

As further illustrated in FIG. 6, as pressure is applied to the plunger 602, the plunger 602 presses the cell mixture 612 through the cell substrate 604. This mechanical pressure forces cells deep into the cell substrate 604. Furthermore, due in part to the viscosity of the cell mixture 612 more cells land and adhere to the cell substrate 604. Accordingly, outflow 614 contains few cells.

As mentioned, in some implementations, the disclosed method comprises utilizing a vacuum to seed the cells. In one example, the cell mixture 612 and the cell substrate 604 are placed in a sealed container. Air in the sealed container is removed by vacuum, which forces the cell mixture 612 into the pores of the cell substrate 604. For example, as illustrated in FIG. 6, a vacuum may be applied to the outlet 616 of the container. The vacuum evacuates the barrel 610 and pulls the cell mixture 612 through the cell substrate 604.

By using different ratios of protein and carbohydrate sources, cross-linker, and cross-linking methods, the disclosed method can form cell substrates with different characteristics. FIGS. 7A-7C illustrate images showing cell substrates created using the disclosed methods in accordance with one or more embodiments of the present disclosure. FIG. 7A and the corresponding paragraphs detail how changing the composition of various components can be used to beneficially tune the organoleptic and food functional properties of a cell-based-meat product. In particular, FIG. 7A illustrates cell substrates 702, cell substrate 704, seeded substrate 706, and seeded substrate 708 formed using different compositions of proteins, carbohydrates, and sodium alginate concentrations.

The cell substrates 702 illustrated in FIG. 7A, for example, comprises cell substrate formed using a cell substrate solution comprising protein, gum mix, and sodium alginate (SA). More specifically, the cell substrates 702 are formed using a cell substrate solution comprising 7% whey (W) protein, a 1% gum mix, and SA. The cell substrates 702, when cooked, has a papery texture. By contrast, the cell substrate 704 is formed using a cell substrate solution comprising protein, modified potato starch (MPS), acetic acid, and SA. More specifically, the cell substrate 704 is made of 4% soy protein powder (S), 1% MPS, 0.5% acetic acid, and 0.5% SA. The cell substrate 704, when cooked falls apart easily and has limited structure.

FIG. 7A also illustrates seeded substrates. More specifically, FIG. 7A illustrates the seeded substrate 706 seeded with lobster cells and the seeded substrate 708 seeded with scallop cells. The seeded substrate 706 comprises protein, MPS, acetic acid, sodium alginate, and is seeded with cells. More specifically, the seeded substrate 706 comprises 4% soy protein powder, 1% MPS, 0.5% acetic acid, 0.5% SA, and cells. The composition of the cell substrate solution used to grow the seeded substrate 706 may result in a texture of cell-based scallop meat more similar to conventional scallop meat than the cell substrate solution used to form the cell substrates 702, the cell substrate 704, and the seeded substrate 708. The seeded substrate 708 is grown using a cell substrate solution comprising protein, MPS, SA, and is seeded with cells. More specifically, the seeded substrate 708 comprises 4% soy protein powder, 0.5% SA, 1% MPS, and cells. The seeded substrate 708, when cooked, exhibits a yellowish tint (which is shown in a darker shade when depicted in black and white) due to soy and had good visual structure.

FIG. 7A illustrates differences in cell substrates and seeded cell substrates resulting from variations in cell substrate solution compositions. However, other variations in later phases also influence the final cell-based-meat product. More particularly, substances may be added to the cell substrate during the gelating phase when seeded cells are gelated within the cell substrate. For example, methods include adding flavors and/or varying the fattiness by adding fats suspended in the gelating phase. Colorants may be added at various stages to change the color of the cell-based-meat product. The disclosed method may further include changing the texture by varying the concentration of the gelating phase or the addition of materials suspended in the gelating phase. Nutritional properties can also be controlled by supplementing nutrients in the gelating phase. With these methods, a common cell substrate may be readily modified during the processing phase to produce multiple cell-based tissue analogs of slaughtered meats, reducing processing costs and increasing the versatility of the cell substrate.

FIG. 7B portrays structural differences in a cell substrate formed using a temperature gradient and an unseeded cell substrate formed using both wettability and temperature gradients. FIG. 7B illustrates a cross-section image 710 and a longitudinal-section image 712 of a cell substrate formed using a temperature gradient. As shown by the arrows in the cross-section image 710, use of the temperature gradient results in the construction of a porous substrate. The arrows in the cross-section image 710 show porous structures within a cell substrate. The longitudinal-section image 712 also shows porous structures throughout the cell substrate. But the porous structures in the longitudinal-section image 712 exhibit a relatively random orientation of fibers in comparison to fibers of a longitudinal-section image 716 of a cell substrate formed using both wettability and temperature gradients, as described further below.

As described previously, a wettability gradient facilitates the formation of layers of cell substrate. More specifically, the combination of the wettability gradient with the temperature gradient forms parallel tubes of honeycomb-like fibrous structures. FIG. 7B illustrates a cross-section image 714 and the longitudinal-section image 716 of a cell substrate formed using both wettability and temperature gradients. As shown, the cross-section image 714 shows the fibrous structures vertically aligned across a cross-section. Furthermore, the longitudinal-section image 716 further shows alignment of the fibrous structures along the Z-axis. As further illustrated in FIG. 7B, the columns are aligned perpendicular to the wettability gradient and parallel to the temperature gradient.

FIG. 7C illustrates images showing structural similarities between an unseeded cell substrate formed by the disclosed method and slaughtered lobster meat. The image 718 and the image 720 portray slaughtered lobster meat. The image 722 and the image 724 portray a cell substrate formed utilizing both temperature and wettability gradients. As shown in the images 718-720, slaughtered lobster meat exhibits a fibrous texture and is composed of muscle fibers that run in parallel through the meat. The muscle fibers in the slaughtered lobster meat depicted in the images 718-720 are aligned along a Z-axis. The images 722-724 demonstrate structural similarities between the cell substrate and the slaughtered lobster meat. More specifically, the cell substrate also demonstrates a fibrous texture with columnar structures aligned along the z-axis.

Figure 8A:
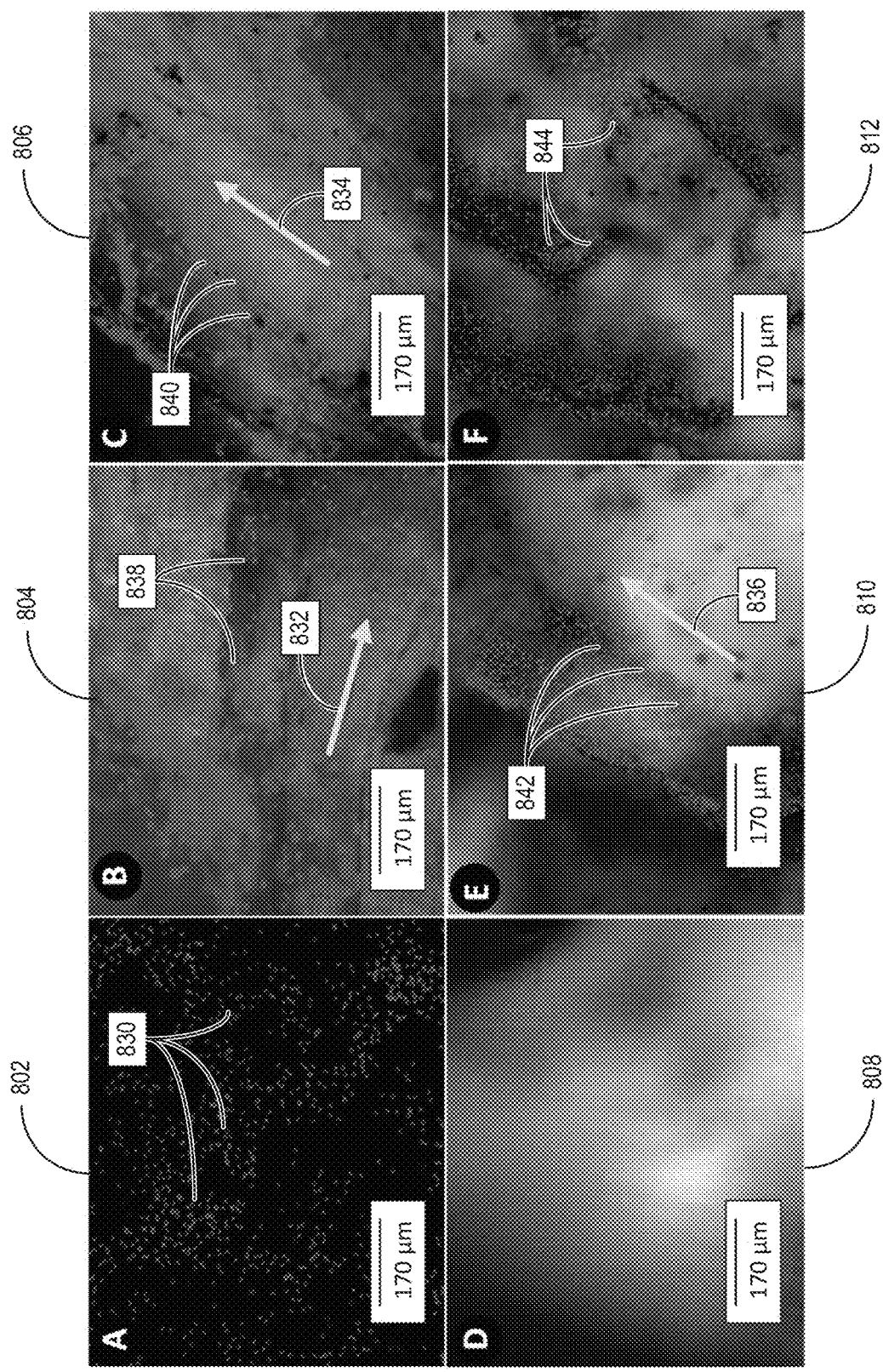
FIGS. 8A-8B illustrate fluorescent microscopic images of nucleolus-stained unseeded and seeded cell substrates and slaughtered lobster and chicken meat in accordance with one or more embodiments of the present disclosure.
Figure 8B:
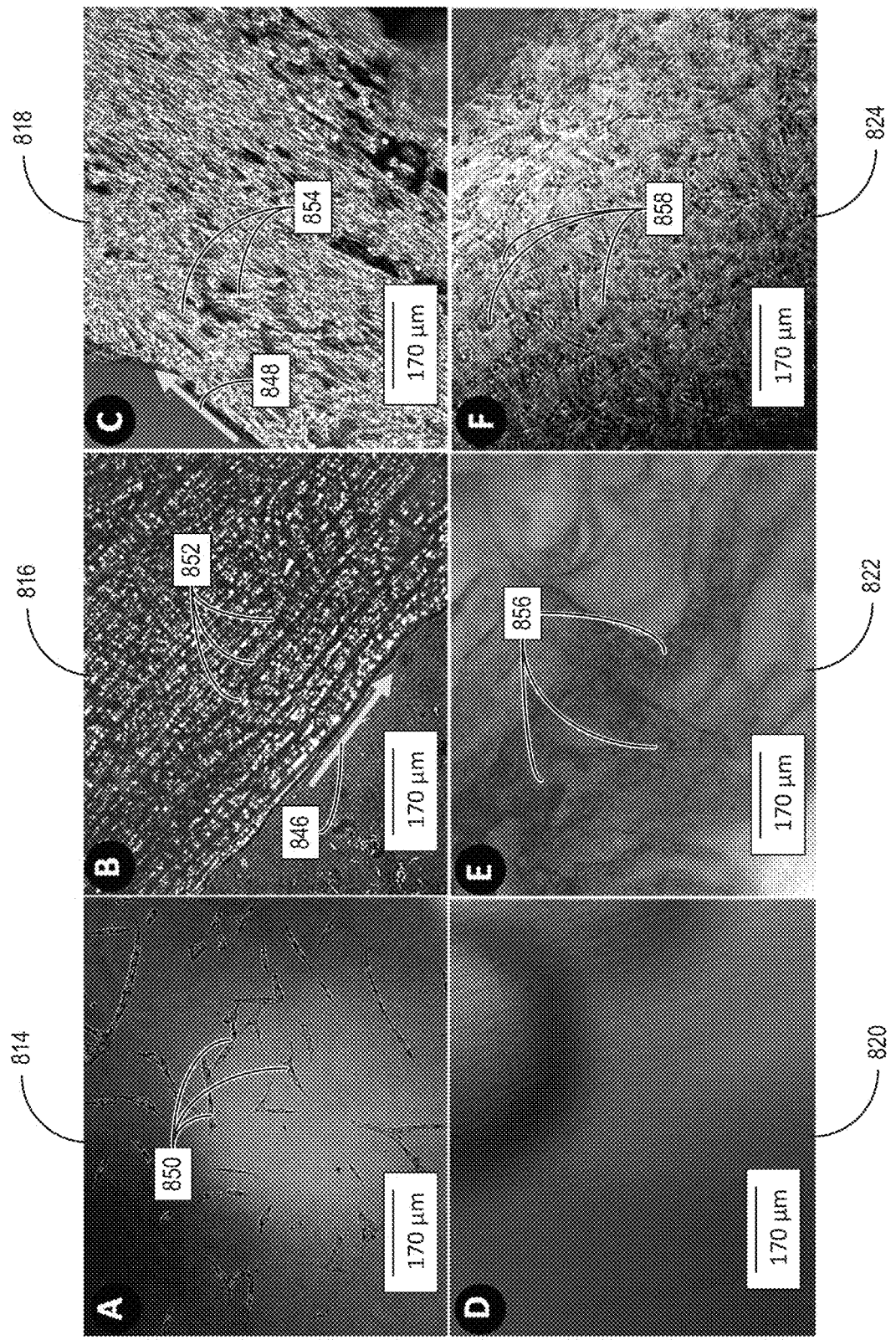

As described previously, the disclosed method may comprise seeding a cell substrate with cells of different types. FIGS. 8A-8B illustrate fluorescent microscopic images of nucleolus-stained unseeded and seeded cell substrates and slaughtered lobster meat in accordance with one or more embodiments of the present disclosure. FIG. 8A illustrates fluorescent microscopic images of cell substrate seeded with lobster cells, and FIG. 8B illustrates fluorescent microscopic images of cell substrate seeded with chicken cells. The lobster cells and the chicken cells shown in FIGS. 8A-8B comprise cells cultured in a culture system.

FIG. 8A portrays different types of lobster cells including lobster hematopoietic stem cells and lobster hemocytes seeded on various types of scaffolds in comparison with slaughtered lobster muscle tissue. The nuclei of the various cells are stained blue in the images illustrated in FIG. 8A, where the blue stain is shown as a lighter shade when depicted in black and white. An image 802 portrayed in FIG. 8A demonstrates nuclei staining of lobster hematopoietic stem cells. More particularly, the blue dots (or lighter shade dots in black and white) shown in the image 808 comprise stained nuclei. For example, the image 802 depicts stained nuclei 830. The lobster hematopoietic stem cells captured in the image 802 are not seeded on a cell substrate and demonstrate successful staining of the cellular nuclei for fluorescent microscopic imaging. The locations of the lobster hematopoietic stem cells are random as they are unseeded on a cell substrate.

As further shown in FIG. 8A, the cell substrate does not stain blue. An image 808 portrays an unseeded cell substrate that has undergone the staining process. The image 808 shows an absence of blue staining (or absence of lighter shaded dots in black and white relative to images 804, 806, 810, and 812). As shown in the image 808, the fluorescent imaging dye does not bind to the cell substrate.

FIG. 8A includes an image 804 of slaughtered lobster muscle tissue. As shown in the image 804, the stained nuclei are arranged in an aligned fibrous structure. For example, stained nuclei 838 are arranged in a fibrous structure. More specifically, the slaughtered lobster cells are arranged in fibers that run parallel to an arrow 832 depicted in the image 804. The image 804 shows how the muscle fibers in slaughtered lobster muscle tissue are visible at microscopic levels.

As mentioned, cell substrates formed using a temperature gradient may be porous but lack structural organization. The image 812 in FIG. 8A depicts lobster hemocytes seeded on a cell substrate formed using only a temperature gradient. As shown in the image 812, the nuclei of the lobster hemocytes do not show any sort of alignment and are randomly distributed throughout the cell substrate. For example, stained nuclei 844 are randomly distributed throughout the cell substrate.

In contrast, cells seeded in cell substrates formed using both wettability and temperature gradients show alignment in parallel fibrous structures. For example, an image 806 and an image 810 depict different types of lobster cells seeded in cell substrates formed using wettability and temperature gradients. The image 806 shows lobster hematopoietic stem cells seeded on a cell substrate formed using wettability and temperature gradients. The image 806 depicts stained nuclei 840 of lobster hematopoietic stem cells. The lobster hematopoietic stem cells are arranged in structures that run parallel to an arrow 834 depicted in the image 806.

The image 810 shows lobster hemocytes seeded on a cell substrate formed using wettability and temperature gradients. For example, the image 810 depicts stained nuclei 842 of lobster hemocytes. As shown, the lobster hemocytes are arranged in structures that run parallel to an arrow 836. Both the lobster hematopoietic stem cells and the lobster hemocytes depicted in the image 806 and the image 810, respectively, show a similar arrangement in parallel fibrous structures to the slaughtered lobster muscle cells shown in the image 804.

The cell substrates depicted in the images 806-810 are formed in tubular molds having a 20 mm diameter and a 4 mm height. For each cell scaffold depicted, the cells were suspended in a 0.5% sodium alginate solution at a concentration of approximately $3 \times 10^6/\mu L$. Approximately 1 mL of the cell-sodium alginate solution was added to each of the cell substrates.

FIG. 8B portrays different chicken fibroblast cells seeded on various types of scaffolds in comparison with slaughtered chicken muscle tissue. The nuclei of the chicken cells are stained blue in the images illustrated in FIG. 8B, where the blue stain is shown as a lighter shade when depicted in black and white. An image 814 portrayed in FIG. 8B demonstrates nuclei staining of chicken cells. More particularly, the blue structures (or lighter shaded structures when depicted in black and white) shown in the image 814 comprise stained cells. For instance, the image 814 depicts stained cells 850. The chicken cells captured in the image 814 are not seeded on a cell substrate and demonstrate successful staining of the cells for fluorescent microscopic imaging. The locations of the chicken cells are random as they are unseeded on a cell substrate.

As further shown in FIG. 8B, the cell substrate does not stain blue. An image 820 portrays an unseeded cell substrate that has undergone the staining process. The image 820 shows an absence of blue staining and cell structures because the fluorescent imaging dye does not bind to the cell substrate.

FIG. 8B includes an image 816 of slaughtered chicken muscle tissue. As shown in the image 816, the stained cells are arranged in an aligned fibrous structure. For example, the image 816 depicts stained cells 852. More specifically, the slaughtered chicken cells are arranged in fibers that run parallel to an arrow 846 depicted in the image 816. The image 816 shows how the muscle fibers in slaughtered chicken muscle tissue are visible at microscopic levels.

As mentioned, cell substrates formed using a temperature gradient may be porous but lack structural organization. The image 822 in FIG. 8B depicts chicken fibroblast cells seeded on a cell substrate formed using only a temperature gradient. For example, the image 822 depicts stained cells 856. As shown, the chicken cells lack alignment. The cell substrate formed using only a temperature gradient portrayed in the image 822 lacks the aligned structure shown in the image 816 depicting the slaughtered chicken meat.

Similarly, cells seeded in a hydrogel fail to demonstrate an aligned fibrous structure. An image 824 in FIG. 8B portrays chicken fibroblast cells seeded in a collagen hydrogel. As shown, the hydrogel may contain pores and a random structure but does not have the fibrous alignment present in slaughtered chicken muscle tissue. More specifically, the image 824 depicts stained cells 858 in a relatively random arrangement in comparison to the stained cells 852 depicted in the image 816.

In contrast to the cells imaged in the image 822, chicken cells seeded in cell substrates formed using both wettability and temperature gradients show alignment in parallel fibrous structures. For example, an image 818 depicts chicken fibroblast cells seeded in a cell substrate formed using wettability and temperature gradients. The image 818 depicts an arrangement of stained cells 854 in a cell substrate. Similar to the slaughtered chicken muscle tissue shown in the image 816, the chicken fibroblast cells shown in the image 818 are aligned along parallel fibrous structures that run parallel to an arrow 848.

The cell scaffolds portrayed in the images 818-820 are formed in cylinder-shaped molds having a 20 mm diameter and a 4 mm height. For each cell scaffold depicted, the cells were suspended in neutralized collagen at a concentration of approximately $3 \times 10^6/\mu L$.

Figure 9A:
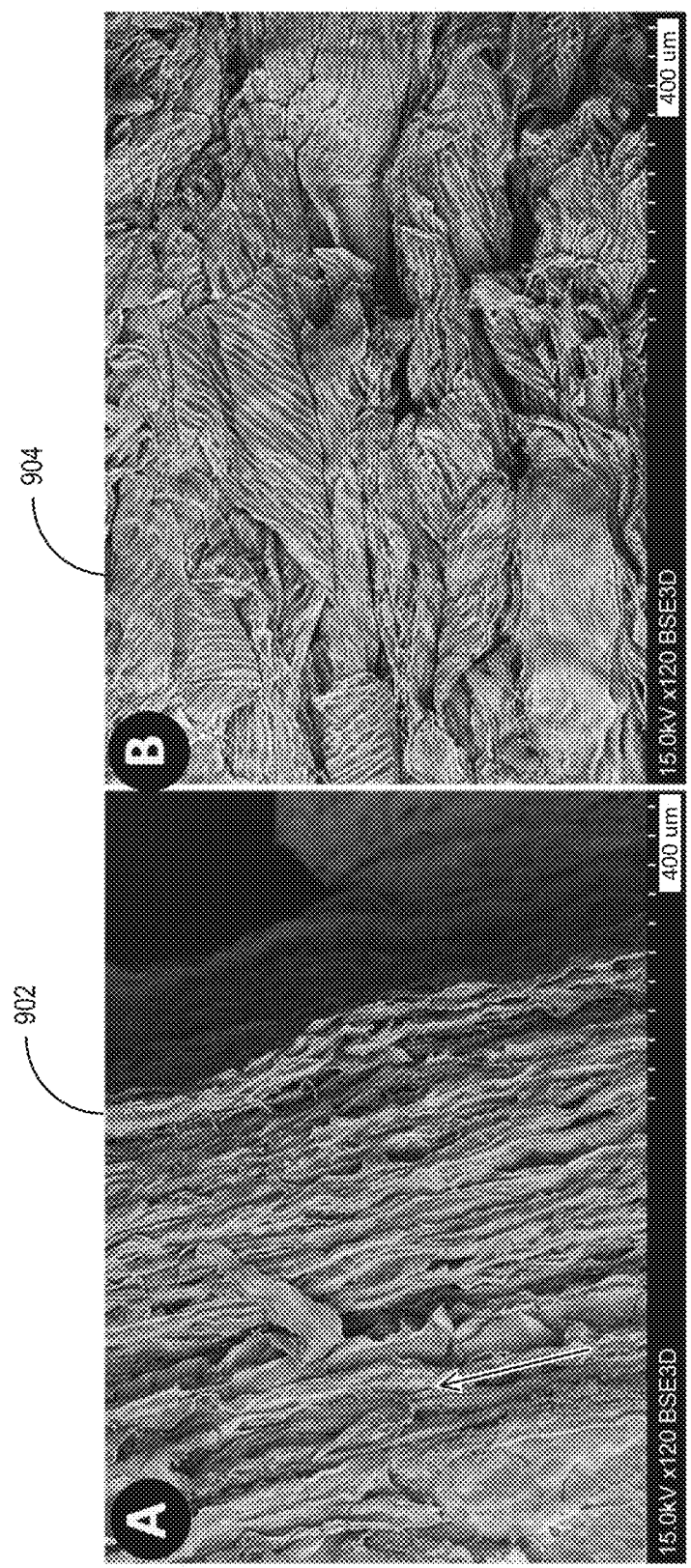
FIGS. 9A-9B depict Scanning Electron Microscope (SEM) images of unseeded and seeded cell substrates in accordance with one or more embodiments of the present disclosure.
Figure 9B:
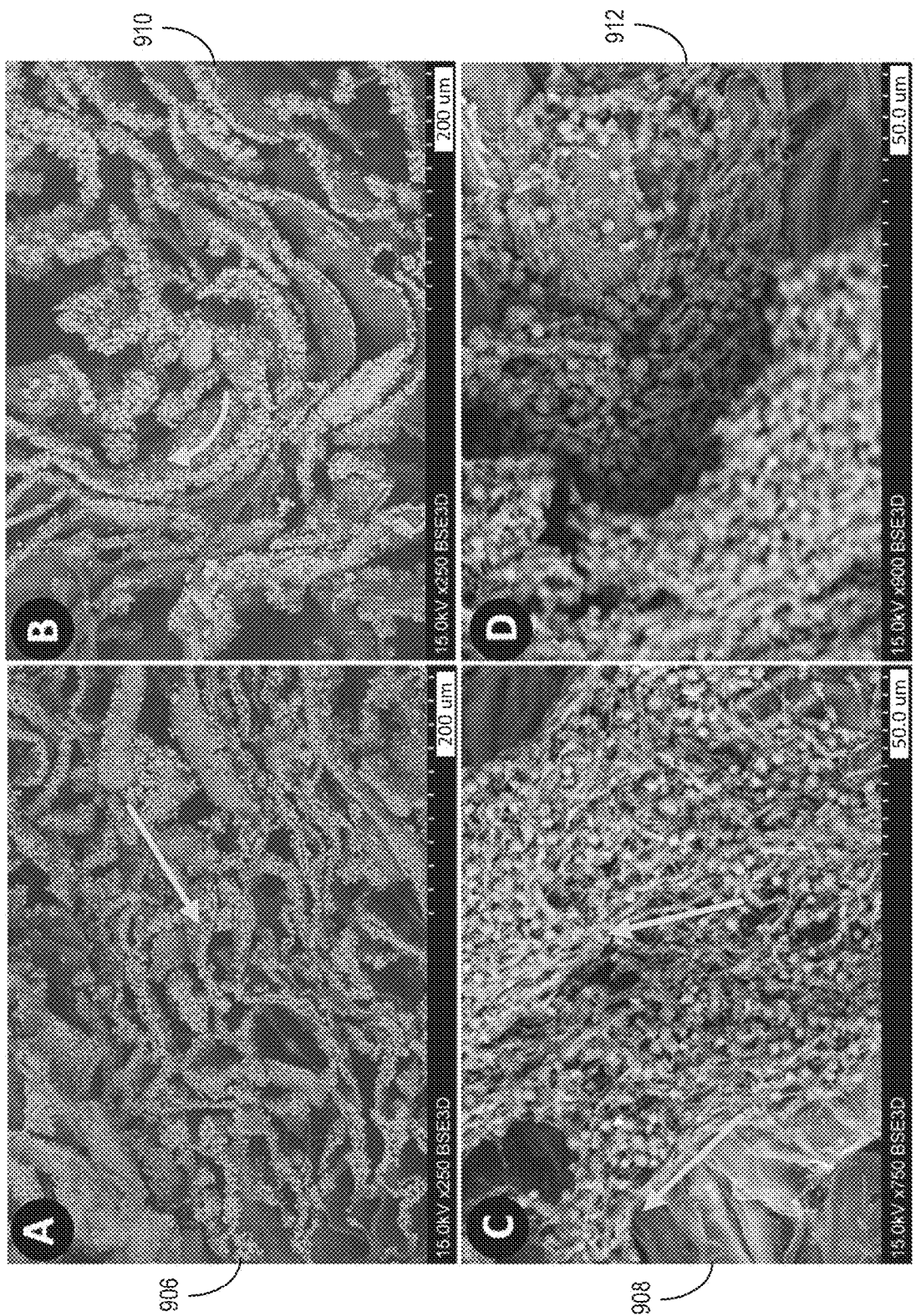

Scanning Electron Microscope (SEM) of the cell substrate formed using wettability and temperature gradients also show fibrous aligned structures characteristic of slaughtered animal muscle tissue. FIGS. 9A-9B depict SEM images of unseeded and seeded cell scaffolds in accordance with one or more embodiments of the present disclosure. FIG. 9A depicts SEM images of unseeded cell scaffolds formed using wettability and temperature gradients and a temperature gradient. FIG. 9B depicts SEM images of seeded cell scaffolds formed using wettability and temperature gradients and a temperature gradient. As used herein, the term "wettability-temperature cell substrate" refers to a cell substrate formed using both wettability and temperature gradients in accordance with one or more embodiments of the present disclosure. The term "temperature cell substrate" refers to a cell substrate formed using only a temperature gradient but no wettability gradient.

FIG. 9A illustrates a comparison between structures of an unseeded wettability-temperature cell substrate with an unseeded temperature cell substrate in accordance with one or more embodiments of the present disclosure. The cell substrates portrayed in FIG. 9A were dehydrated for SEM imaging. FIG. 9A includes an image 902 comprising an SEM image of a longitudinal section of an unseeded wettability-temperature cell substrate. For comparison, FIG. 9A also includes an image 904 comprising an SEM image of a longitudinal section of an unseeded temperature cell substrate. The wettability-temperature cell substrate depicted in the image 902 demonstrates bundles of fibers in a parallel alignment. More specifically, the fibers in the image 902 run parallel to the arrow shown in the image 902. In contrast, the temperature cell substrate depicted in the image 904 shows a random orientation of fibers.

FIG. 9B illustrates SEM images of a seeded wettability-temperature cell substrate and a seeded temperature cell substrate at different magnification levels. FIG. 9B includes an image 906 of a seeded wettability-temperature cell substrate at a first magnification and an image 908 of the seeded wettability-temperature cell substrate at a second magnification. FIG. 9B also includes an image 910 of a seeded temperature cell substrate at a first magnification and an image 912 of the seeded temperature cell substrate at a second magnification. The SEM images portrayed in FIG. 9B were taken from cell substrates seeded with lobster hemocytes. The seeded cell substrates were dehydrated using an ethanol gradient.

As shown in FIG. 9B, the wettability-temperature cell substrate portrayed in the image 906 has a more linear fibrous structure relative to the temperature cell substrate portrayed in the image 910. The globular structures visible in the image 906 and the image 910 comprise lobster hemocyte nuclei. In the wettability-temperature cell substrate depicted in the image 906, the lobster hemocytes are roughly aligned in an orientation parallel to the arrow. In contrast, the image 910 portrays cells within a temperature cell substrate in a curved alignment.

The image 908 and the image 912 show SEM images of the wettability-temperature cell substrate and the temperature cell substrate at a second and greater magnification level, respectively. At this greater magnification, the image 908 shows the lobster hemocytes oriented in the same plane and in parallel alignment within the wettability-temperature cell substrate. As mentioned previously, the globular structures comprise lobster hemocyte nuclei, and the attached fibrous structure shows an alignment of the cytoplasm and/or hydrogel in the cell substrate. In contrast, the lobster hemocytes seeded on the temperature cell substrate are oriented on different planes. Furthermore, the lobster hemocytes seeded on the temperature cell substrate in the image 912 show no particular alignment.

Figure 10A:
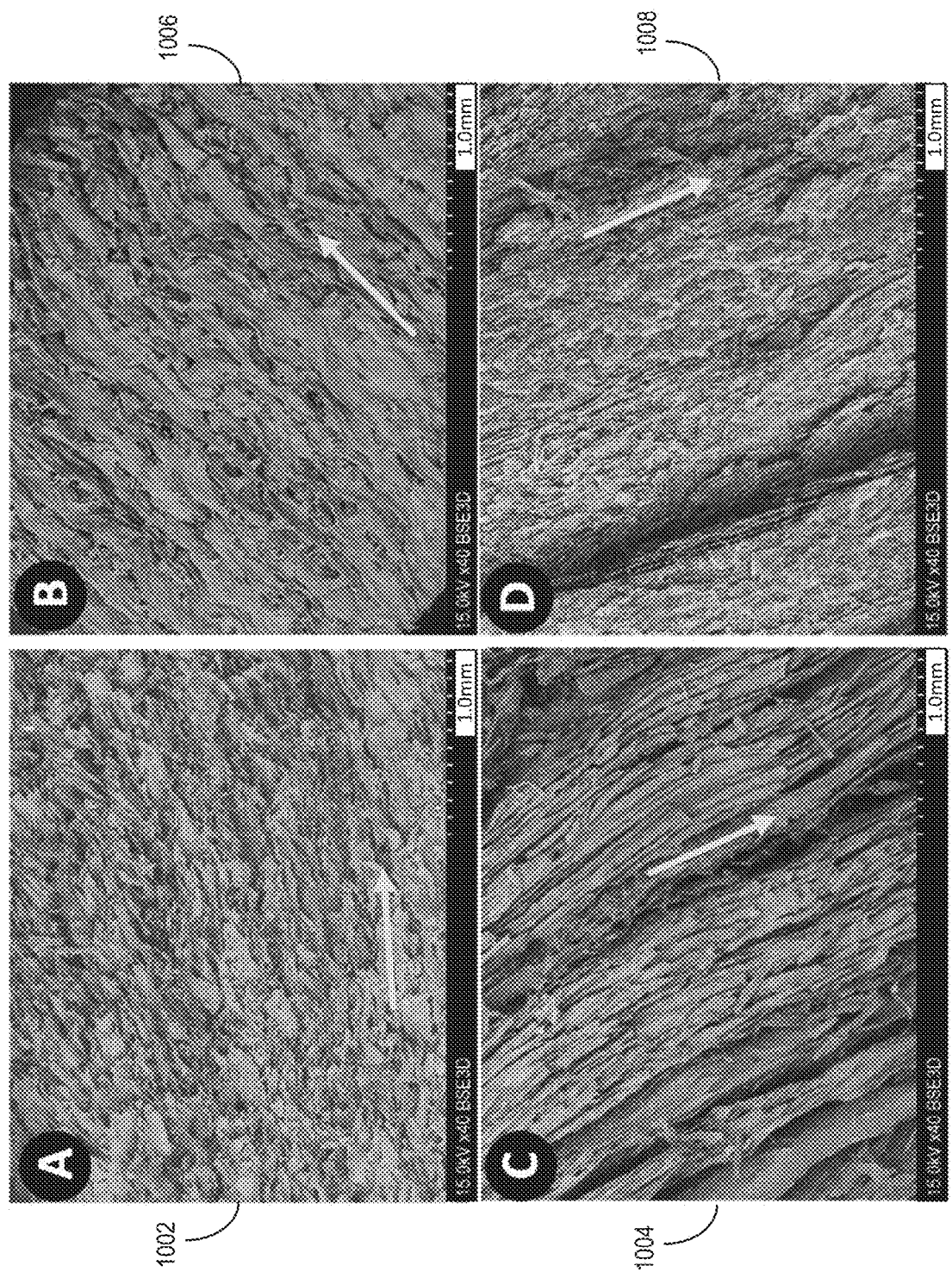
FIGS. 10A-10C depict SEM images that portray structural similarities between cell substrates formed using wettability and temperature gradients and slaughtered acellular muscle fibers in accordance with one or more embodiments of the present disclosure.
Figure 10B:
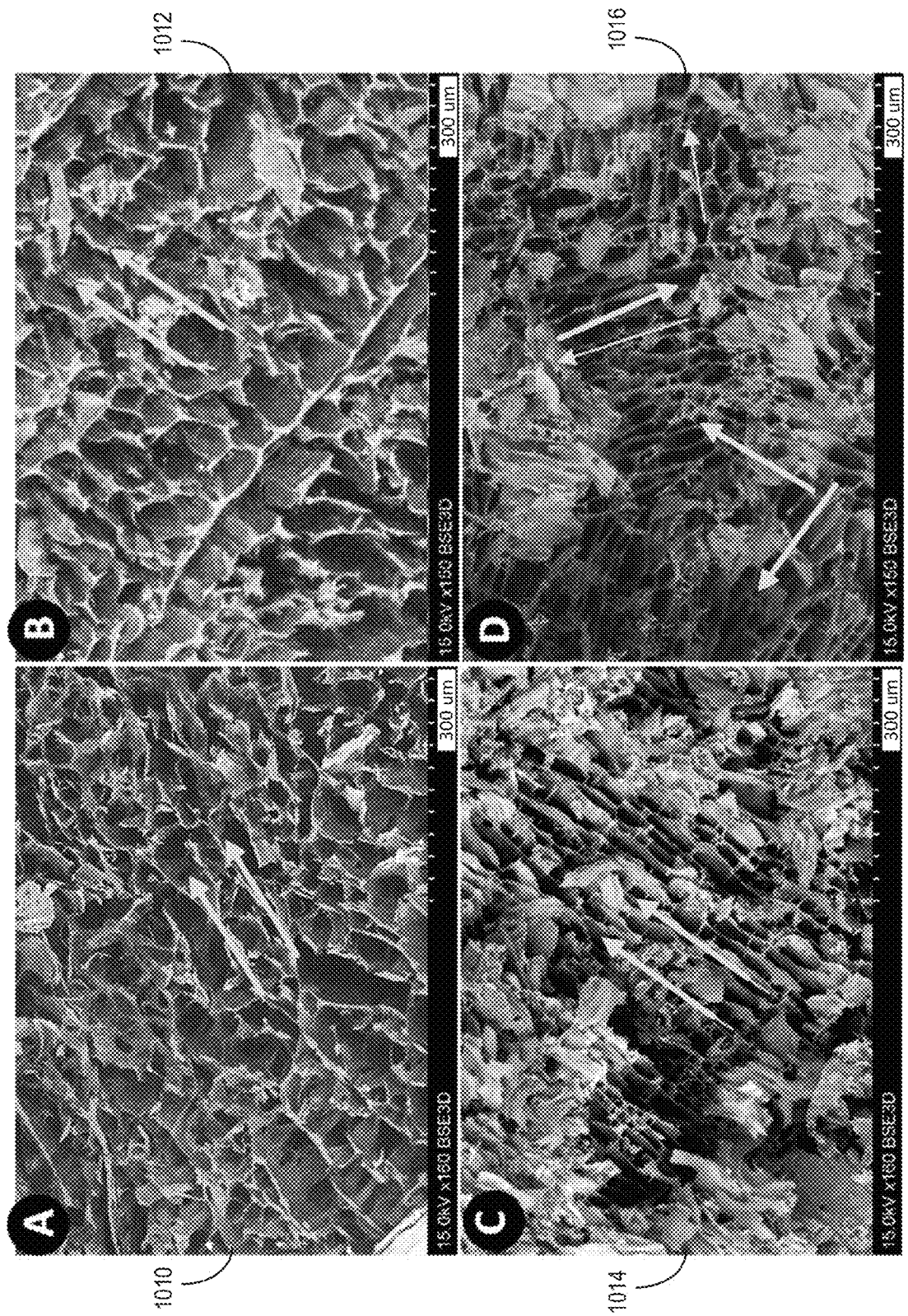
Figure 10C:
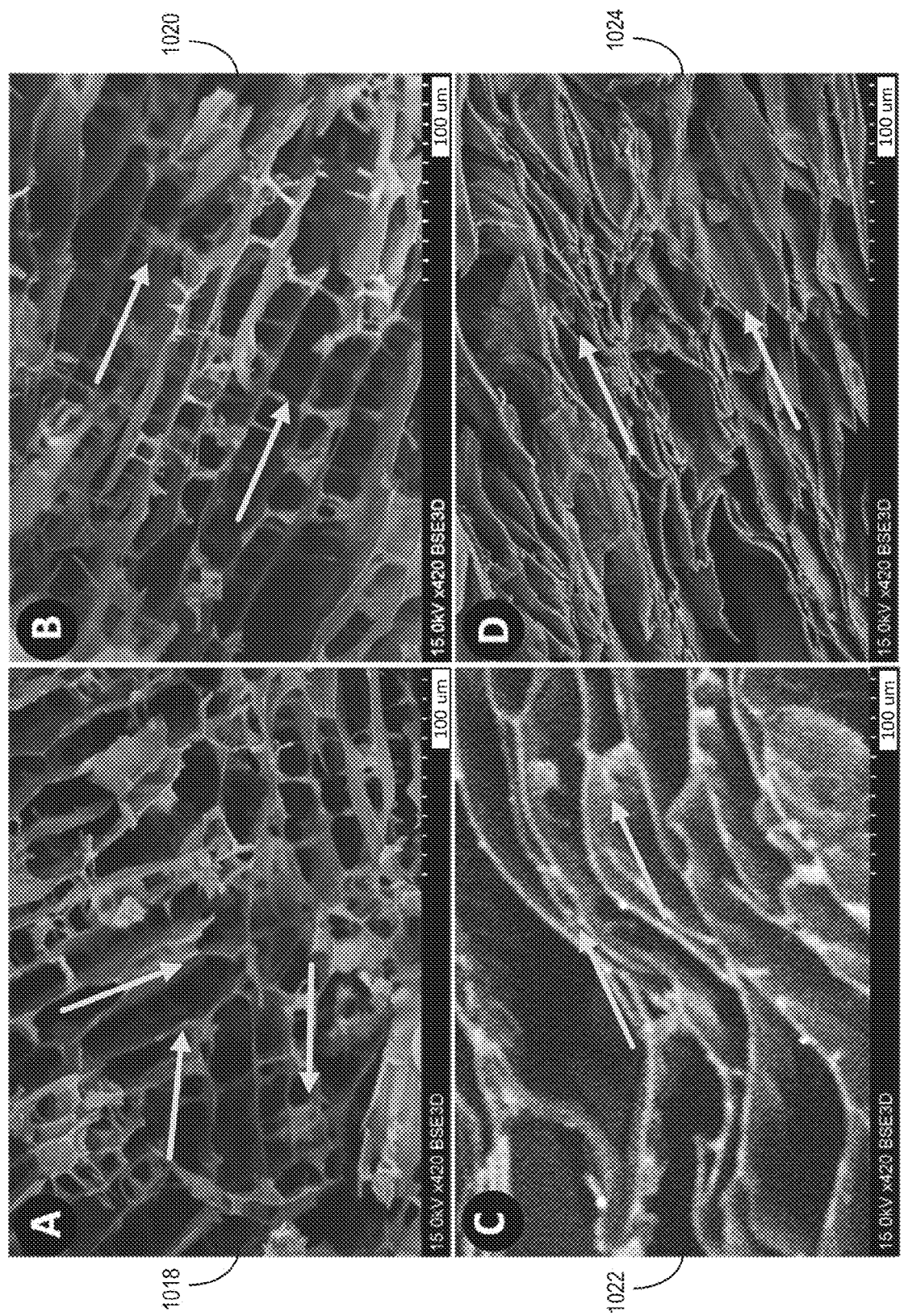

As described previously, wettability gradients can align the orientation of bundles of water crystals to form an alignment of fibers in cell substrates like the alignment of muscle fibers found in slaughtered meat. FIGS. 10A-10C depict SEM images that portray structural similarities between cell substrates formed using wettability and temperature gradients and slaughtered acellular muscle fibers in accordance with one or more embodiments of the present disclosure. FIG. 10A portrays SEM images of longitudinal sections of decellularized slaughtered lobster and slaughtered chicken tissue compared with a wettability-temperature cell substrate. FIG. 10B portrays SEM images of cross sections of decellularized slaughtered lobster muscle and decellularized slaughtered chicken muscle compared with wettability-temperature cell substrate. FIG. 10C portrays SEM images of cross sections of a wettability-temperature cell substrate, a temperature cell substrate, and decellularized slaughtered lobster tissue.

As mentioned, FIG. 10A portrays SEM images of longitudinal sections of decellularized slaughtered lobster and slaughtered chicken tissue compared with a wettability-temperature cell substrate. FIG. 10A includes an image 1002 and an image 1004 portraying SEM images of longitudinal sections of decellularized slaughtered meat. More specifically, the image 1002 depicts acellular slaughtered lobster meat. The image 1004 depicts acellular slaughtered chicken meat. The slaughtered meat samples depicted in the images 1002-1004 were prepared for imaging by decellularization using sodium deoxycholate and DNAse 1(1). The samples were then frozen and dried using a freeze drier. The acellular samples depicted in the images 1002-1004 show the structure of the extracellular matrix without cells. The cell substrates formed using the disclosed method are meant to mimic the structure of the extracellular matrix of slaughtered meat.

FIG. 10A includes an image 1006 and an image 1008 comprising SEM images of wettability-temperature cell substrates formed in accordance with one or more implementations of the current disclosure. The image 1006 portrays a longitudinal section of a wettability-temperature cell substrate formed in a tube mold (e.g., the mold portrayed in FIG. 3A). The image 1008 portrays a longitudinal section of a wettability-temperature cell substrate formed in a lobster tail mold (e.g., the mold portrayed in FIGS. 3B-3C). As shown in FIG. 10A, the wettability-temperature cell substrate depicted in the images 1006-1008 display an alignment of fibers that closely mimic the alignment fibers of acellular slaughtered lobster meat depicted in the image 1002 and the acellular slaughtered chicken meat depicted in the image 1004.

FIG. 10B depicts SEM images of cross sections of the tissues portrayed in FIG. 10A. FIG. 10B includes an image 1010 of acellular slaughtered lobster meat, an image 1012 of acellular slaughtered chicken meat, an image 1014 of a wettability-temperature cell substrate, and an image 1016 of a temperature cell substrate. As with the slaughtered meat samples shown in FIG. 10A, the acellular slaughtered lobster meat and the acellular slaughtered chicken meat portrayed in the images 1010-1012 were decellularized using sodium deoxycholate and DNase 1(1). The slaughtered meat samples were then frozen and dried using a freeze drier.

As shown in FIG. 10B, the diameter of the pores in the wettability-temperature cell substrate depicted in the image 1014 is like the diameter of the pores in the acellular slaughtered lobster meat in the image 1010 and the acellular slaughtered chicken meat in the image 1012. Furthermore, the fibers in the wettability-temperature cell substrate portrayed in the image 1014 are oriented in a similar organized fashion to the fibers in the acellular slaughtered lobster meat portrayed in the image 1010 and the acellular slaughtered chicken meat portrayed in the image 1012. In contrast, the fibers in the temperature cell substrate portrayed in the image 1016 do not show uniformity in orientation.

As described previously, changing the rate of freezing can change the size of the pores in the resulting cell substrate. FIG. 10C illustrates comparisons between cell substrates formed in a tube mold as depicted in FIG. 3A, and a lobster tail mold as depicted in FIG. 3B. In particular, FIG. 10C illustrates an image 1018 of a temperature cell substrate formed in a lobster tail mold, an image 1020 of a wettability-temperature cell substrate formed in a lobster tail mold, an image 1022 of a wettability-temperature cell substrate formed in a tube mold, and an image 1024 of acellular slaughtered lobster meat. The images 1018-1024 portrayed in FIG. 10C comprise SEM images of cross sections of the respective samples.

As mentioned, cell substrates formed in lobster tail molds may have smaller pore sizes due to higher rates of freezing. More specifically, because more surface area of the lobster tail mold can be exposed to a cooling agent relative to a surface area of a tube mold exposed to the cooling agent, freezing of cell substrate solution may occur at higher rates within lobster tail molds. In some examples, the freezing rate within a lobster tail mold is about 15 times faster than the freezing rate within a tube mold. As shown in FIG. 10C, the pore size of the wettability-temperature cell substrate formed in the tube mold portrayed in the image 1022 is significantly larger than the pore size of the cell substrates formed in the lobster tail mold portrayed in the image 1018 and the image 1020. Thus, the rate of freezing can be adjusted to more closely mimic the pore size found in acellular slaughtered lobster meat, as depicted in the image 1024.

Furthermore, and as shown in FIG. 10C, wettability-temperature cell substrates display fiber alignment more similar to acellular slaughtered lobster meat. As shown by the arrows in the image 1018, the temperature cell substrate has a random arrangement of fibers. In contrast, and as shown by the arrows in the image 1020 and the image 1022, the wettability-temperature cell substrates formed using the lobster tail mold and the tube mold display a more structured and parallel alignment. The fiber alignment and structure of the wettability-temperature cell substrate more closely resembles the fiber alignment and structure of acellular slaughtered lobster meat depicted in the image 1024.

Figure 11A:
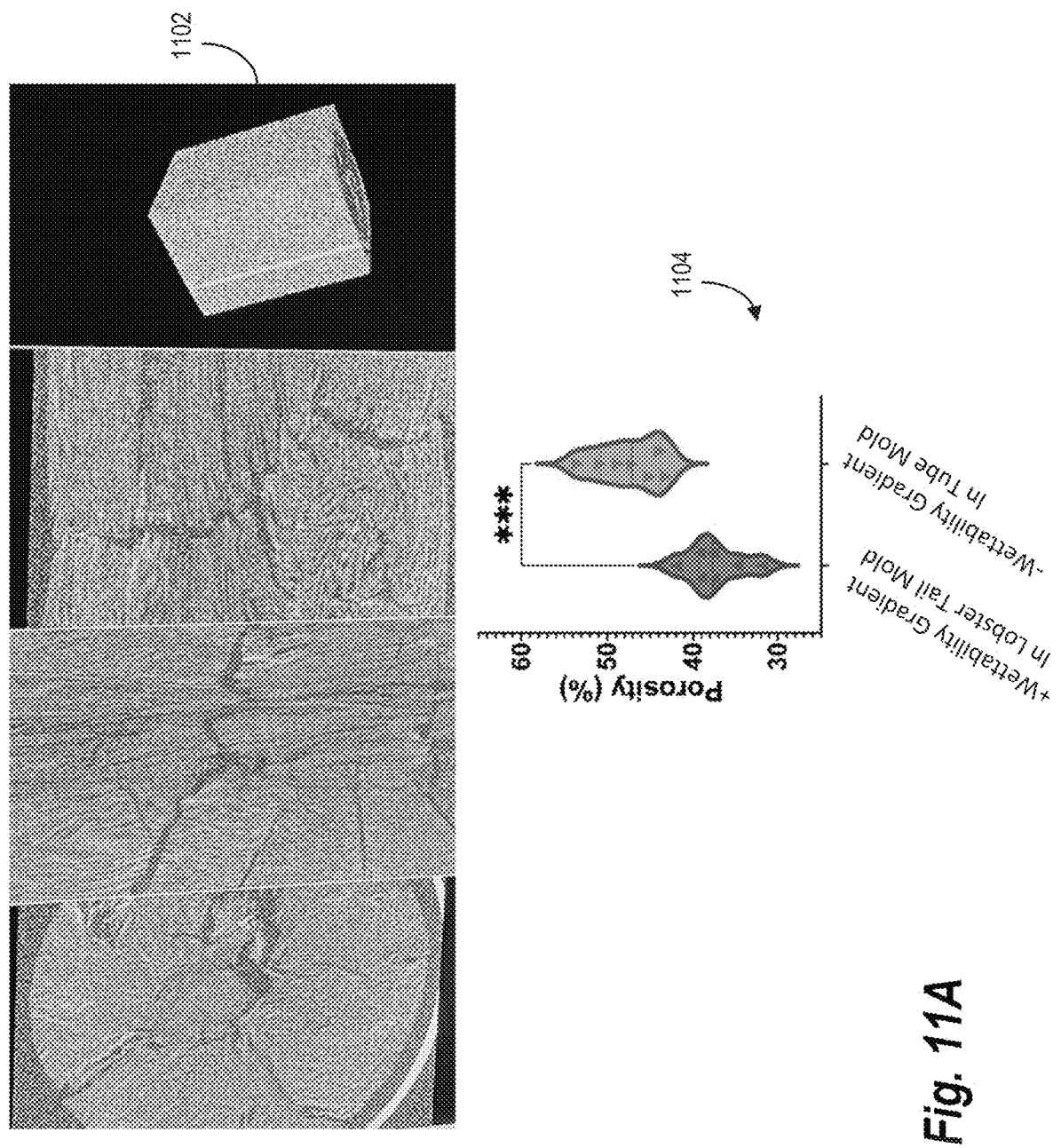
FIGS. 11A-11D images that illustrate adjusting porosity in cell substrates by changing different factors in cell substrate formation in accordance with one or more embodiments of the present disclosure.
Figure 11B:
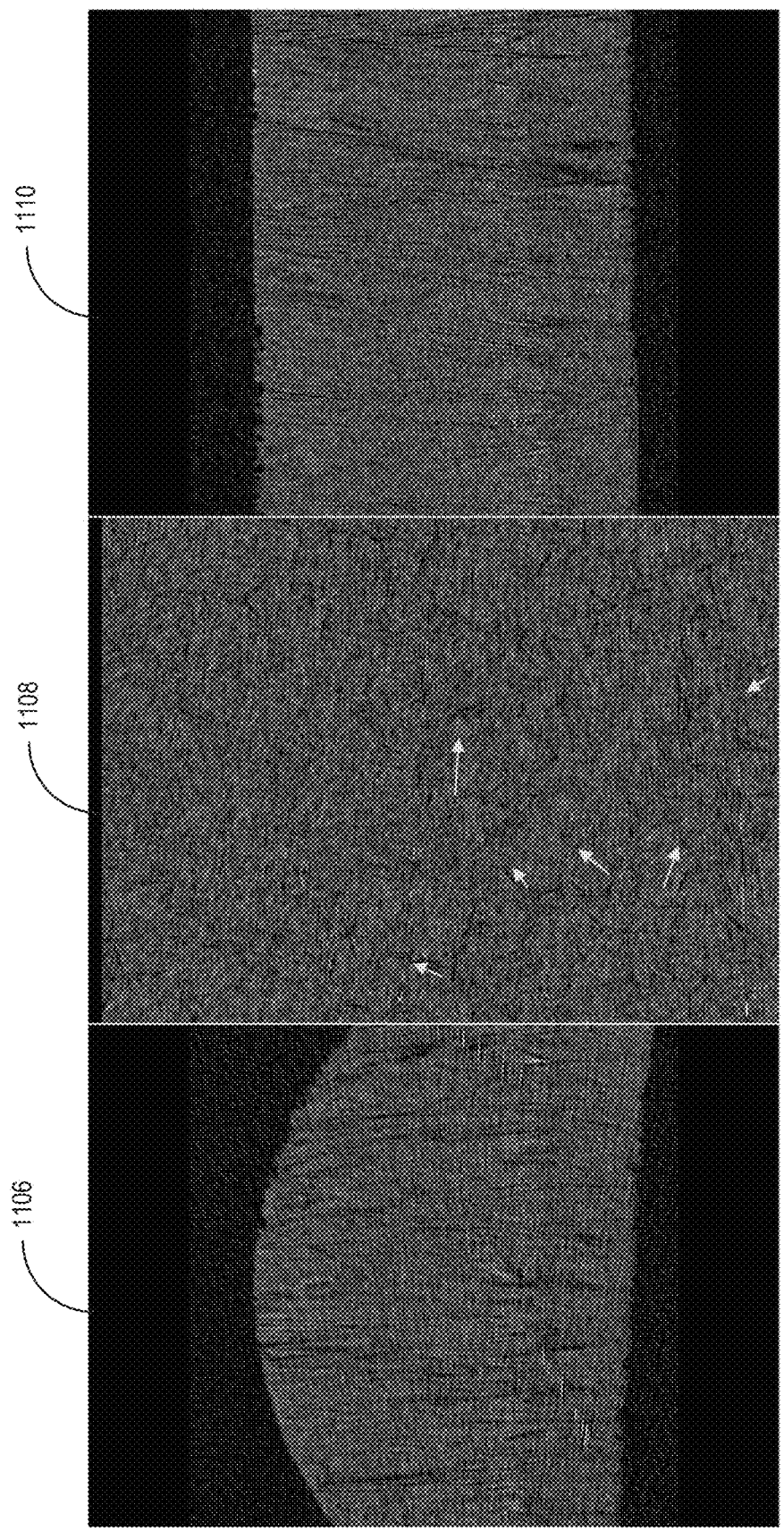
Figure 11C:
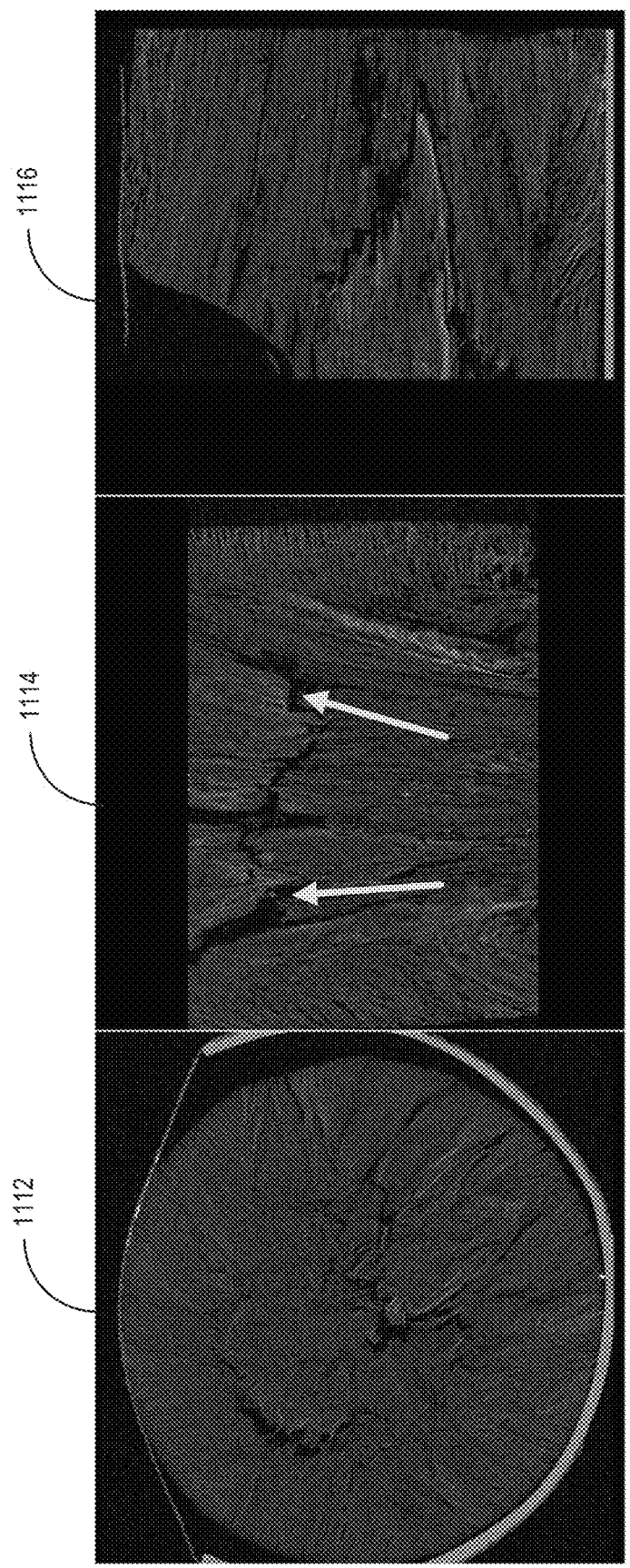
Figure 11D:
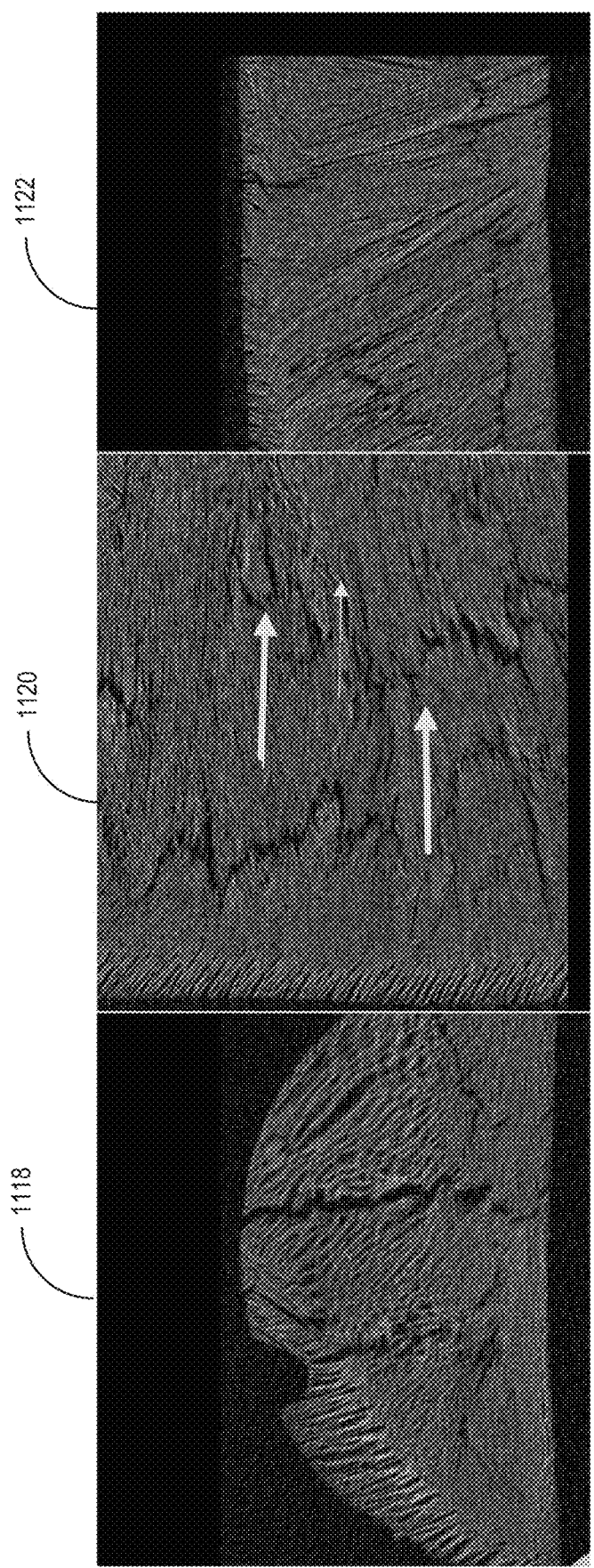

Cell substrates formed using wettability and thermal gradients can demonstrate porosity and greater alignment of the fibers. FIGS. 11A-11D illustrate how porosity in cell substrates can be adjusted by changing different factors in cell substrate formation in accordance with one or more embodiments of the present disclosure. Porosity in cell substrates can be measured using micro-computed tomography (or "u-CT") imaging. FIG. 11A illustrates the porosity of a wettability-temperature cell substrate in a lobster tail mold compared to the porosity of a wettability-temperature cell substrate in a tube mold in accordance with one or more embodiments of the present disclosure. FIG. 11B illustrates u-CT images of a temperature cell substrate in accordance with one or more embodiments of the present disclosure. FIG. 11C illustrates u-CT images of a wettability-temperature cell substrate formed in a tube mold in accordance with one or more embodiments of the present disclosure. FIG. 11D illustrates u-CT images of a wettability-temperature cell substrate formed in a lobster tail mold in accordance with one or more embodiments of the present disclosure.

Generally, porosity refers to the extent to which a material or substance contains void spaces within its structure. Porosity can be quantified by measuring the ratio of pore volume to the total volume of the material and is typically expressed as a percentage. Porosity can be determined utilizing u-CT images. The u-CT images portrayed in FIGS. 11A-11D were captured on cell substrates having Lugol's solution. In some cases, cell substrates imaged without Lugol's solution results in images with high noise content. Thus, Lugol's solution was added to the cell substrate solution for the cell substrates imaged in FIGS. 11A-11D to increase the contrast and imaging quality. Lugol's solution is a dark solution containing iodine and potassium iodide used as a staining agent.

FIG. 11A illustrates the porosity of a wettability-temperature cell substrate in a lobster tail mold compared to the porosity of a wettability-temperature cell substrate in a tube mold in accordance with one or more embodiments of the present disclosure. Pores in images 1102 of a wettability-temperature cell substrate were quantified and plotted using a chart 1104. As shown in the chart 1104, the average porosity for the wettability-temperature cell substrate formed in a tube mold equaled 47.438494%. The average porosity for the wettability-temperature cell substrate formed in the lobster tail mold equaled 37.4786%, indicating less empty space (e.g., pore space) than that formed in the tube mold. Based on these measurements, porosity of a wettability-temperature cell substrate can be adjusted between 30%-60% by changing different factors in cell substrate formation such as changing the rate of temperature and adjusting the cell substrate solution composition.

FIG. 11B illustrates u-CT images of a temperature cell substrate in accordance with one or more embodiments of the present disclosure. The temperature cell substrate depicted in FIG. 11B was formed in a lobster tail mold. FIG. 11B illustrates a cross-section image 1106, a magnified image 1108, and a longitudinal-section image 1110 of the temperature cell substrate. As shown in FIG. 11B, the temperature cell substrate displays limited porosity. Furthermore, the pores highlighted by the arrows in the magnified image 1108 are relatively narrow in width.

In contrast to temperature cell substrates, wettability-temperature cell substrates demonstrate increased porosity and pores of greater size. FIG. 11C illustrates u-CT images of a wettability-temperature cell substrate formed in a tube mold in accordance with one or more embodiments of the present disclosure. FIG. 11C depicts a cross-section image 1112, a magnified image 1114, and a longitudinal-section image 1116 of the wettability-temperature cell substrate formed in the tube mold. As shown by the arrows included in the magnified image 1114, the wettability-temperature cell substrate formed in the tube mold demonstrates more pores and pores of greater size relative to the temperature cell substrate depicted in FIG. 11B. The pores in the wettability-temperature cell substrate formed in the tube mold also demonstrate a strong organizational structure with pores running in parallel to each other.

FIG. 11D illustrates u-CT images of a wettability-temperature cell substrate formed in a lobster tail mold in accordance with one or more embodiments of the present disclosure. FIG. 11D depicts a cross-section image 1118, a magnified image 1120, and a longitudinal-section image 1122 of the wettability-temperature cell substrate formed in the lobster tail mold. As shown by the arrows included in the magnified image 1120, the wettability-temperature cell substrate formed in the lobster tail mold also demonstrate more pores and pores of greater size relative to the temperature cell substrate depicted in FIG. 11B. Furthermore, the u-CT images included in FIG. 11D show a columnar and aligned structure of the pores.

Figure 12A:
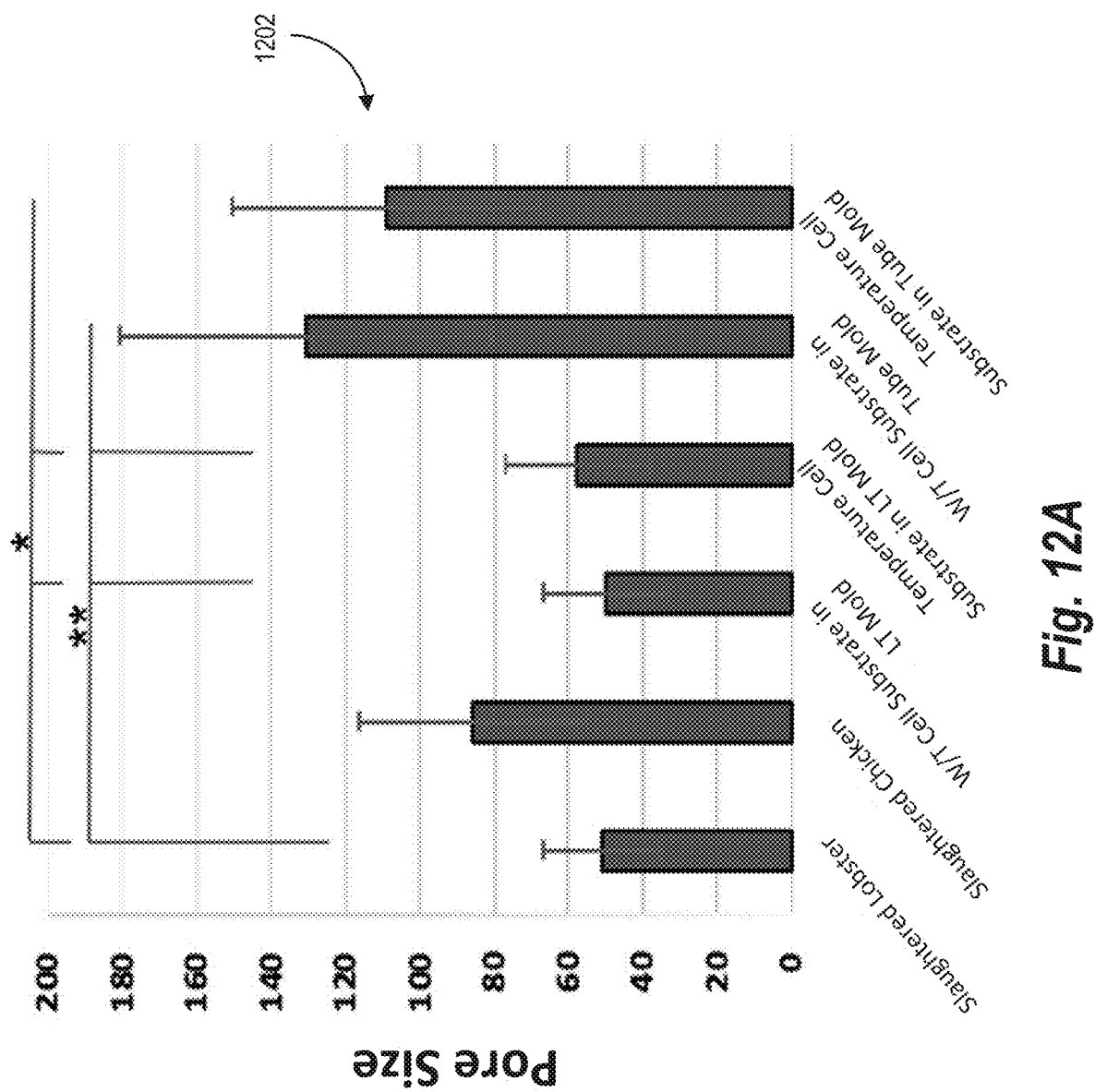
FIGS. 12A-12D illustrate graphs showing distributions of pore size for the cell substrate formed using the disclosed method in accordance with one or more embodiments of the present disclosure.
Figure 12B:
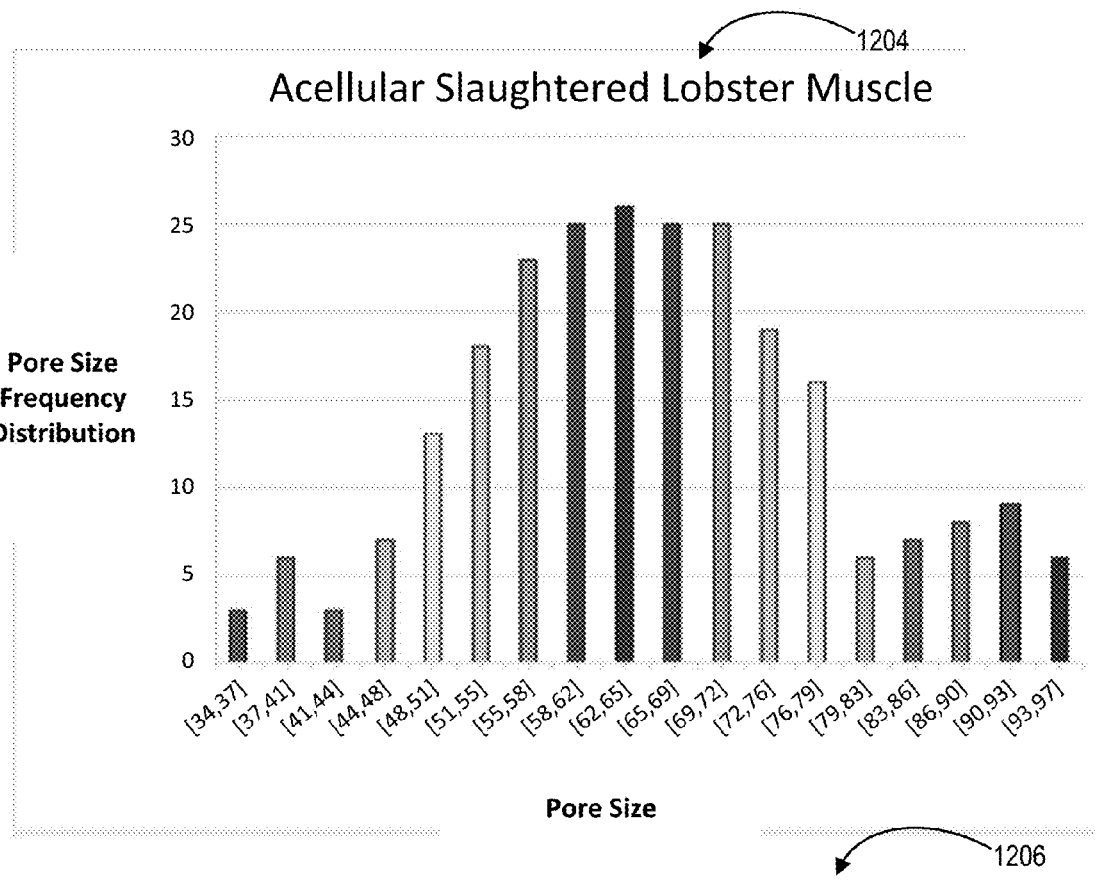
Figure 12B:
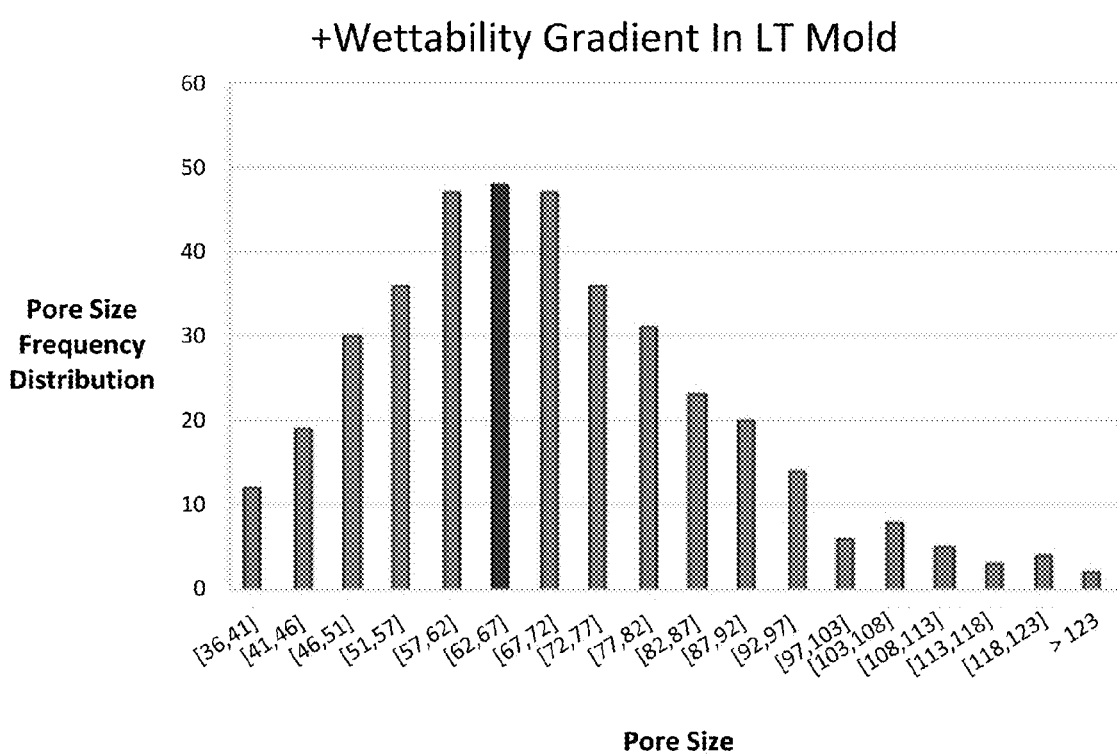
Figure 12C:
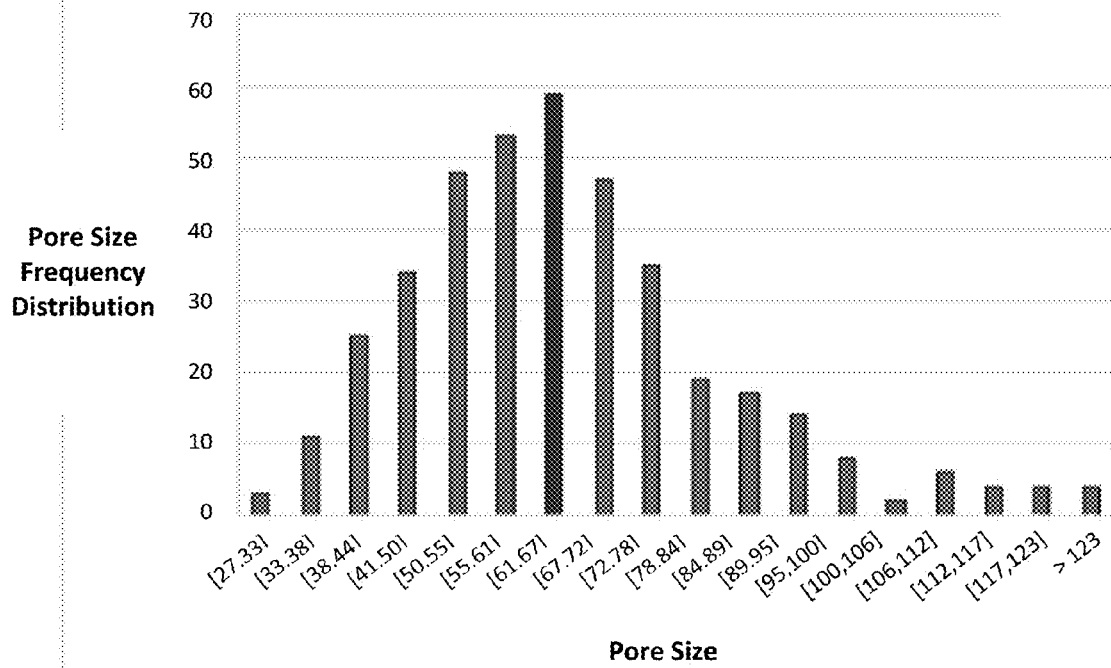
Figure 12C:
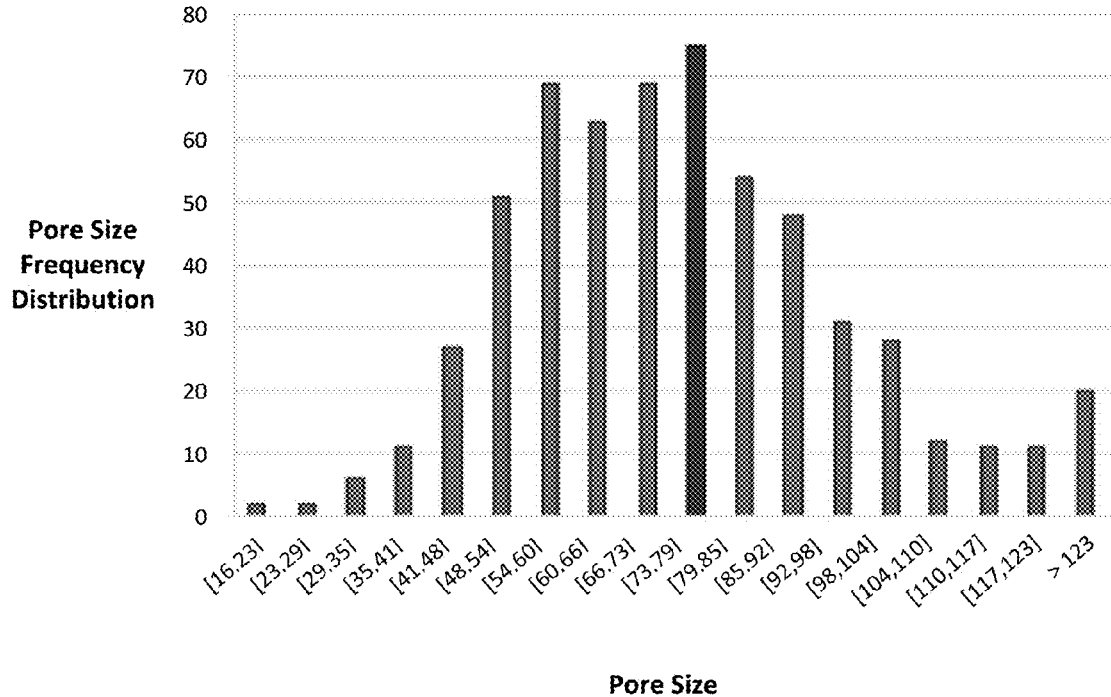
Figure 12D:
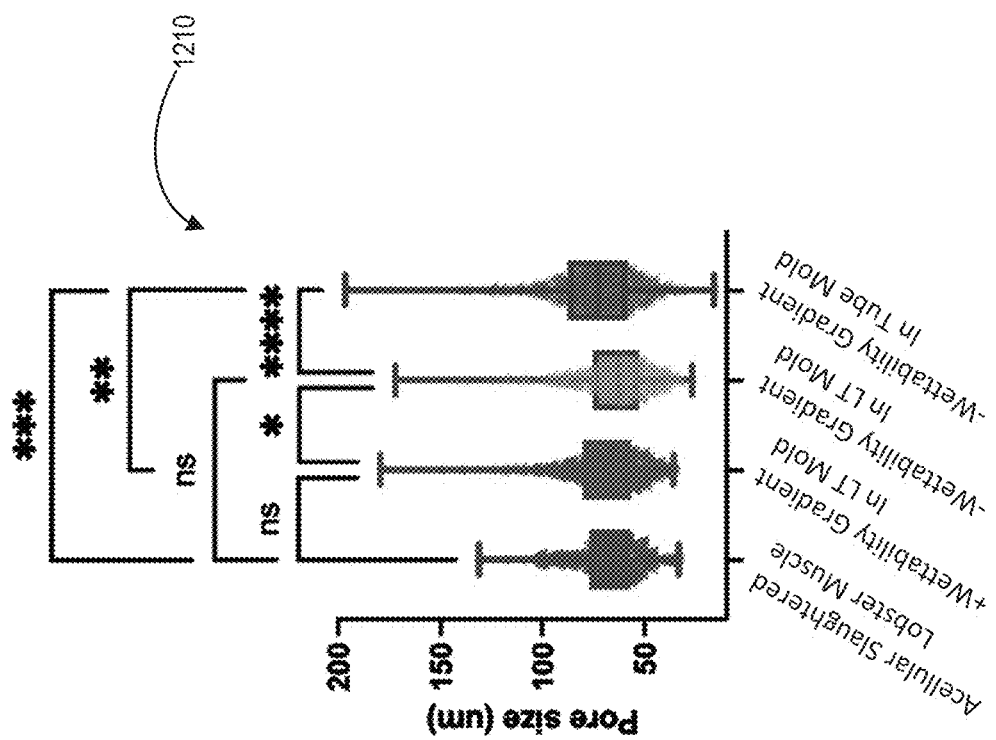

FIGS. 12A-12D illustrate graphs showing distributions of pore size for the cell substrate formed using the disclosed method in accordance with one or more embodiments of the present disclosure. FIG. 12A depicts a graph comparing pore sizes between wettability-temperature cell substrates, temperature cell substrates, and various types of cellular slaughtered meats in accordance with one or more embodiments of the present disclosure. FIG. 12B illustrates a series of graphs comparing distributions in pore sizes between acellular slaughtered lobster muscle and a wettability-temperature cell substrate formed in a lobster tail mold in accordance with one or more embodiments of the present disclosure. FIG. 12C illustrates a series of graphs comparing distributions in pore sizes between temperature cell substrates formed in a lobster tail mold and a tube mold in accordance with one or more embodiments of the present disclosure. FIG. 12D illustrates a box plot comparing the distributions in pore sizes between wettability-temperature cell substrates, temperature cell substrates, and various types of slaughtered meats in accordance with one or more embodiments of the present disclosure.

FIG. 12A depicts a graph 1202 comparing pore sizes between wettability-temperature cell substrates, temperature cell substrates, and various types of slaughtered meats in accordance with one or more embodiments of the present disclosure. The graph 1202 was compiled using data from SEM images. The SEM images were taken of the slaughtered animal meats and cell substrates. Pores shown within the SEM images were measured and plotted in the graph 1202.

As shown, the graph 1202 shows distributions of pore size diameter (in micrometers) in slaughtered lobster muscle, slaughtered chicken muscle, a wettability-temperature (w/t) cell substrate formed in a lobster tail (LT) mold, a temperature cell substrate formed in a lobster tail mold, a wettability-temperature cell substrate in a tube mold, and a temperature cell substrate in a tube mold, respectively. As shown, pore size distribution for the wettability-temperature cell substrate in the lobster tail mold and the temperature cell substrate in the lobster tail mold most closely resembled a distribution of pore size in slaughtered lobster muscle. The pore sizes in cell substrates formed in a tube mold tended to be larger in diameter than pore sizes in slaughtered lobster muscle.

FIG. 12B illustrates a series of graphs comparing distributions in pore sizes between acellular slaughtered lobster muscle and a wettability-temperature cell substrate formed in a lobster tail mold. FIG. 12B portrays a graph 1204 showing a distribution of pore size in acellular slaughtered lobster muscle and a graph 1206 showing a distribution of pore size in wettability-temperature cell substrate (+wettability gradient) formed in a lobster tail mold. As shown in FIG. 12B, the x-axes of the graphs 1204-1206 indicate a pore size in micrometers. The y-axes of the graphs 1204-1206 indicate a pore size frequency.

As shown in the graph 1204, the median pore size is between 62 to 65 micrometers in diameter for acellular slaughtered lobster muscle. The wettability-temperature cell substrate formed in a lobster tail mold most closely matches the distribution of pore size for acellular slaughtered lobster muscle. For example, and as shown in graph 1206, the median pore size is between 62 and 67 micrometers in diameter for the wettability-temperature cell substrate formed in a lobster tail mold. Furthermore, the range in pore size frequency distribution of the wettability-temperature cell substrate formed in the lobster tail mold shown in the graph 1206 encapsulates the range in pore size frequency distribution of the acellular slaughtered lobster muscle. Pore sizes in the wettability-temperature cell substrate formed in the lobster tail mold ranges from 36 to greater than 123 micrometers, and pore sizes in the acellular slaughtered lobster muscle ranges from 34 to 97 micrometers.

FIG. 12C portrays a graph 1207 showing a distribution of pore size in temperature cell substrate (-wettability gradient) formed in a lobster tail mold, and a graph 1208 showing a distribution of pore size in a temperature cell substrate formed in a tube mold. The temperature cell substrates demonstrate some similarities in pore size distribution with a pore size distribution within acellular slaughtered lobster muscle.

A box plot 1210 illustrated in FIG. 12D further demonstrates the similarities in distributions in pore sizes between acellular slaughtered lobster muscle and a wettability-temperature cell substrate formed in a lobster tail mold. The results depicted in FIG. 12D portray various pore sizes from different samples. In particular, for each sample, an average pore size is measured from 600 pores at 6 different depths for each sample. As shown in the box plot 1210, differences between the distribution in pore size for acellular slaughtered lobster muscle and the wettability-temperature cell substrate formed in the lobster tail mold is not significant (annotated by "ns"). As further shown, differences between pore sizes in the temperature cell substrate formed in the lobster tail mold and the acellular slaughtered lobster muscle are also not significant. The asterisk (*) annotations in the box plot 1210 indicate p-value. A single asterisk (*) indicates a p-value of less than 0.05, two asterisks () indicate a p-value of less than 0.001, three asterisks (*) indicate a p-value of less than 0.001, and four asterisks (****) indicate a p-value of less than 0.0001.

As shown by the graphs 1207-1208 in FIG. 12C and the box plot 1210 illustrated in FIG. 12D, pore sizes for the temperature cell substrate formed in a lobster tail mold and a tube mold tend to run larger than pore sizes for the acellular slaughtered lobster muscle. A distribution of pore size in a temperature cell substrate formed in a tube mold is significantly different than the distribution of pore size in acellular slaughtered lobster muscle.

Figure 13:
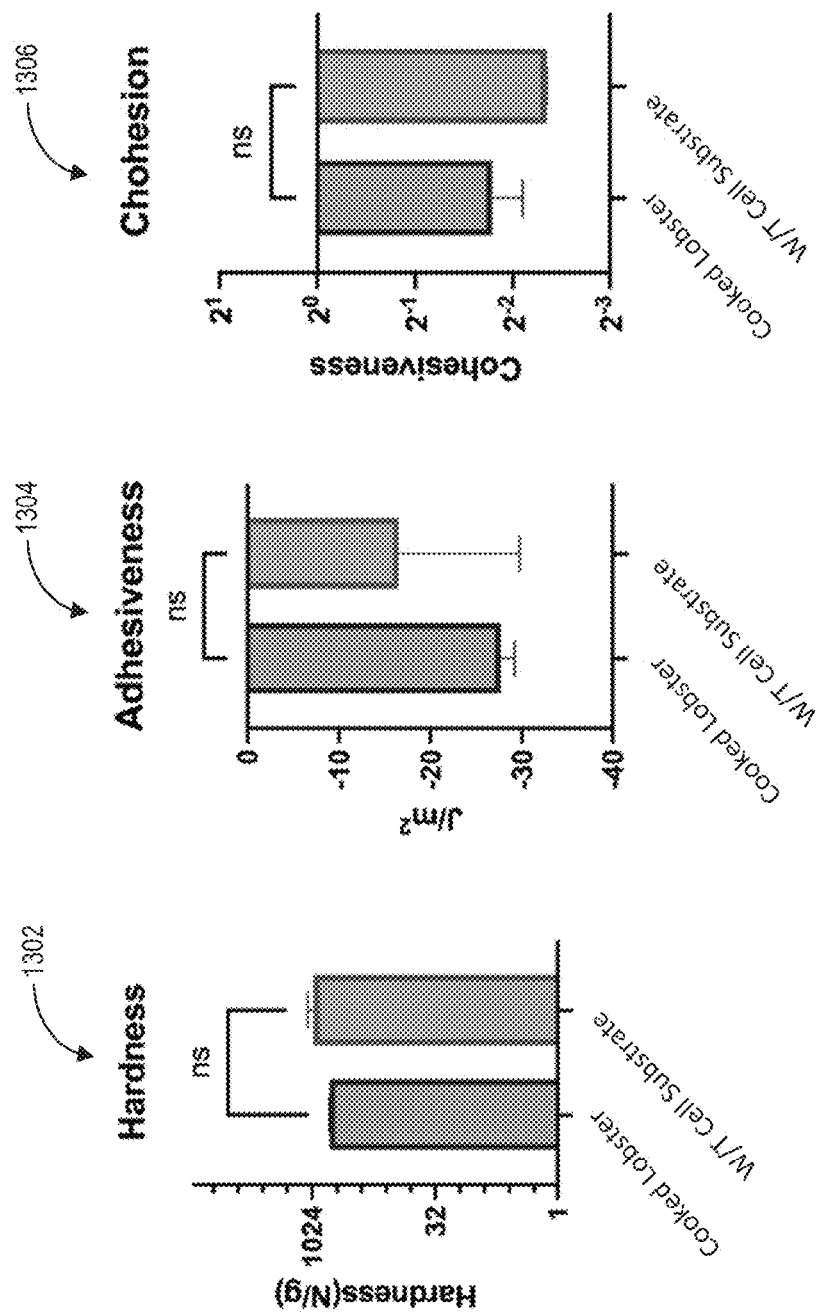
FIG. 13 illustrates graphs demonstrating textural similarities between cooked slaughtered lobster meat and cell substrates formed using wettability and temperature gradients in accordance with one or more embodiments of the present disclosure.

FIGS. 7A-12B above demonstrated structural similarities between acellular slaughtered lobster muscle and wettability-temperature cell substrates produced by the disclosed methods. In addition to structural similarities, wettability-temperature cell substrates produced by the disclosed methods demonstrate textural similarities with cooked slaughtered lobster meat. FIG. 13 illustrates a series of graphs demonstrating textural similarities between cooked slaughtered lobster meat and cell substrates formed using wettability and temperature gradients in accordance with one or more embodiments of the present disclosure. FIG. 13 illustrates results of a texture profile analysis (TPA). FIG. 13 illustrates a chart 1302 depicting hardness, a chart 1304 depicting adhesiveness, and a chart 1306 depicting cohesion. As shown, wettability-temperature cell substrates have non-significant differences in texture profiles with cooked slaughtered lobster meat.

As described above with relation to FIG. 5, the disclosed method may comprise seeding cells in a cell substrate and hydrogel hybrid. The cell substrate can be formed using wettability and thermal gradients. Cells are seeded into the cell substrate and gelated into place with a hydrogel. The wettability-temperature cell substrate tested for the charts 1302-1306 comprises a cell substrate comprising soy protein, sodium alginate, and starch. Lobster hemocyte cells are gelated into place using a hydrogel comprising of sodium alginate.

The chart 1302 shows similarities in hardness between cooked slaughtered lobster meat and a wettability-temperature cell substrate. Hardness is a measure of the force required to compress or deform a material. In TPA, hardness is quantified as the peak force needed to penetrate or compress a sample. As shown in FIG. 13, the cooked slaughtered lobster meat has a hardness of approximately 1020 Newtons per gram (N/g). The wettability-temperature cell substrate has a similar hardness.

The chart 1304 shows similarities in adhesiveness between cooked slaughtered lobster meat and a wettability-temperature cell substrate. Adhesiveness refers to the tendency of a material to stick to surfaces or other materials. In TPA, adhesiveness is measured as the negative force or work required to separate a texture analyzer from the sample surface during the test. As shown in FIG. 13, the cooked slaughtered lobster meat has an adhesiveness of approximately $-27$ Joules per square meter ($J/m^2$). The adhesiveness for the wettability-temperature cell substrate measures at about $-15$ $J/m^2$, which is not considered a significant difference.

FIG. 13 further illustrates the chart 1306 demonstrating similarities on cohesion between cooked slaughtered lobster meat and a wettability-temperature cell substrate. Cohesion describes the internal strength or tendency of a material to stick together. In TPA, cohesion is assessed by evaluating the ability of a sample to maintain its structure during deformation. It is measured by parameters such as springiness and chewiness. As shown by the chart 1306, both the cohesiveness of the cooked slaughtered lobster meat and the cohesiveness of the wettability-temperature cell substrate measure approximately $2^{-2}$.

Figure 14:
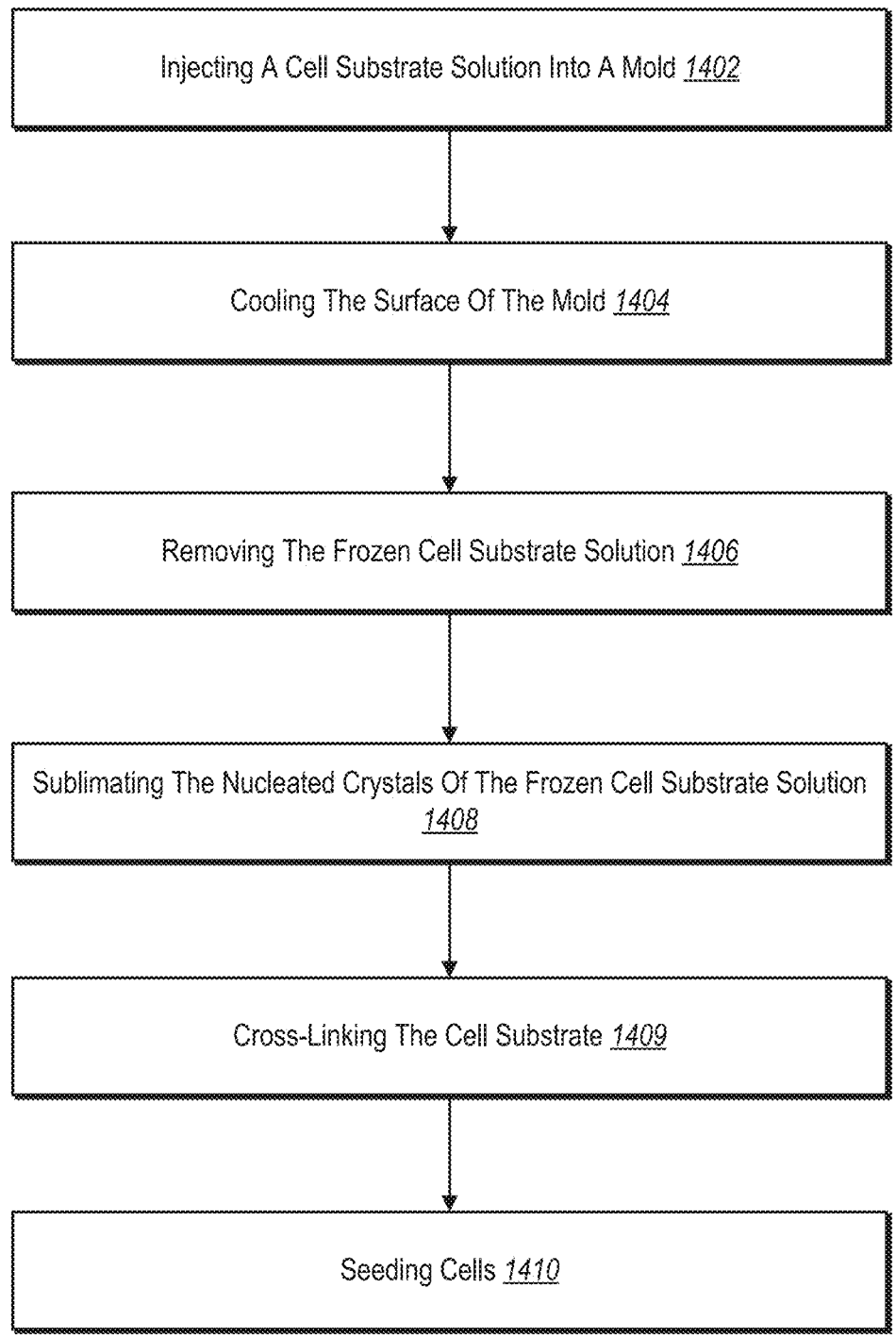
FIG. 14 illustrates a series of acts for forming and seeding a cell substrate in accordance with one or more embodiments.
Figure 15:
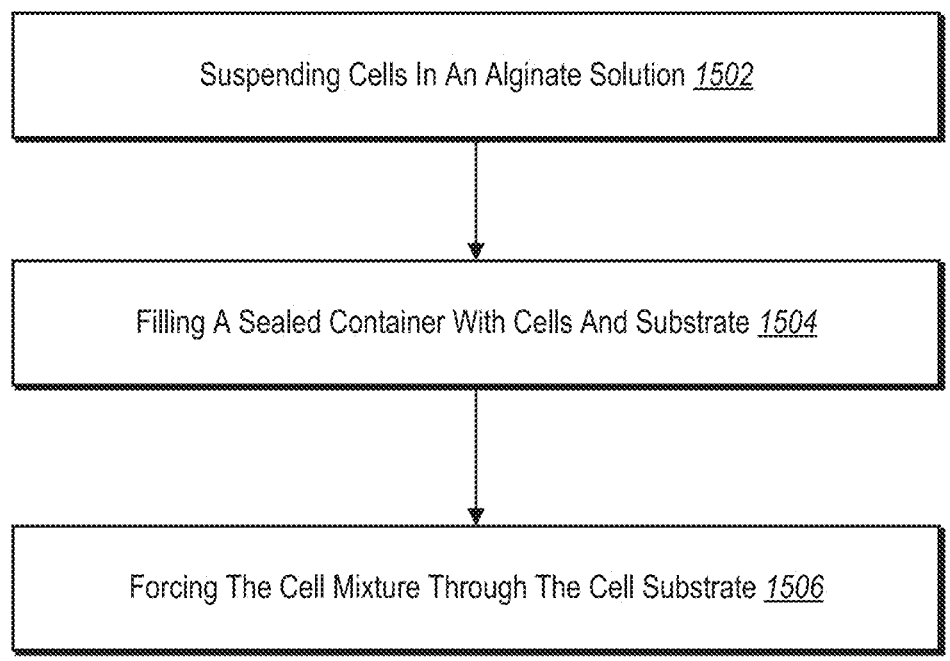
FIG. 15 illustrates a series of acts for seeding a structured porous cell substrate in accordance with one or more embodiments.

FIGS. 1-13, the corresponding text, and the examples provide several different systems, methods, techniques, components, and/or devices relating to forming a structured porous cell substrate in accordance with one or more embodiments. In addition to the above description, one or more embodiments can also be described in terms of flowcharts including acts for accomplishing a particular result. FIGS. 14-15 illustrate such flowcharts of acts. The acts described herein may be repeated or performed in parallel with one another or in parallel with different instances of the same or similar acts. By way of overview, FIG. 14 illustrates a series of acts including an act 1402 of injecting a cell substrate solution into a mold, an act 1404 of cooling the surface of the mold, an act 1406 of removing the frozen cell substrate solution, an act 1408 of sublimating the nucleated crystals of the frozen cell substrate solution, an act 1409 of cross-linking the cell substrate, and an act 1410 of seeding cells.

The series of acts 1400 illustrated in FIG. 14 includes the act 1402 of injecting a cell substrate solution into a mold. In particular, the act 1402 comprises injecting a cell substrate solution into a mold comprising a surface having a wettability gradient. In some embodiments, the mold comprises two semi-cylindrical compartments. In some embodiments, the mold comprises a cylindrical compartment. Additionally, in some embodiments, the mold comprises a metal surface having the wettability gradient and one or more additional plastic surfaces. In some examples, the mold comprises silicone extensions to form large pores in the cell substrate.

The series of acts 1400 comprises the act 1404 of cooling the surface of the mold. In particular, the act 1404 comprises cooling the surface of the mold to freeze the cell substrate solution, form a temperature gradient within the mold, and nucleate crystals. In some implementations, the act 1404 further comprises cooling the surface of the mold by applying a cooling agent to the metal surface, wherein the cooling agent comprises at least one of dry ice or liquid nitrogen. In one or more embodiments, the act 1404 further comprises insulating the mold prior to cooling the surface of the mold by applying insulating materials to the one or more additional plastic surfaces of the mold.

As further illustrated in FIG. 14, the series of acts 1400 includes the act 1406 of removing the frozen cell substrate solution. In particular, the act 1406 comprises removing the frozen cell substrate solution from the mold.

The series of acts 1400 further includes the act 1408 of sublimating the nucleated crystals of the frozen cell substrate solution. In particular, the act 1408 comprises sublimating the nucleated crystals of the frozen cell substrate solution to form a cell substrate.

In some implementations, the series of acts 1400 includes the act 1409 of cross-linking the cell substrate. In particular, the series of acts 1400 can include cross-linking and/or washing the cell substrate in preparation for seeding. In some embodiments, the act 1409 is an optional act and may be omitted from the series of acts 1400.

The series of acts 1400 further includes the act 1410 of seeding cells. In particular, the act 1410 comprises seeding cells onto the cell substrates. In some implementations, the act 1410 further comprises seeding cells onto the cell substrate by: suspending cells in an alginate solution to form a cell mixture, filling a sealed container with the cell mixture and the cell substrate, and forcing the cell mixture through the cell substrate to seed cells throughout the cell substrate. Furthermore, in some implementations, the act 1408 comprises seeding cells onto the cell substrate by: flowing cells of a first cell type comprising at least one of myocytes, adipocytes, or fibroblasts through the cell substrate, flowing cells of a second cell type comprising at least one of myocytes, adipocytes, or fibroblasts through the cell substrate, and gelating the cells of the first cell type and the cells of the second cell type.

The series of acts 1400 can further comprise an additional act of gelating the seeded cells by immersing the cell substrate and the seeded cells in a lobster saline solution.

FIG. 15 illustrates a series of acts for seeding a cell substrate. By way of overview, FIG. 15 illustrates a series of acts 1500 comprising an act 1502 of suspending cells in an alginate solution, an act 1504 of filling a sealed container with cells and substrate, and an act 1506 of forcing the cell mixture through the cell substrate.

FIG. 15 illustrates the act 1502 of suspending cells in an alginate solution. In particular, the act 1502 comprises suspending cells in an alginate solution to form a cell mixture.

The series of acts 1500 illustrated in FIG. 15 also includes the act 1504 of filling a sealed container with cells and substrate. In some implementations, the act 1504 further comprises filling the sealed container by: adding, to the sealed container, a first cell substrate comprising a porous matrix having pores of a first size; and layering, on top of the first cell substrate in the sealed container, a second cell substrate comprising a porous matrix having pores of a second size.

FIG. 15 further illustrates the act 1506 of forcing the cell mixture through the cell substrate. In particular, the act 1506 comprises forcing the cell mixture through the cell substrate to seed cells throughout the cell substrate. In some implementations, the act 1506 further comprises forcing the cell mixture through the cell substrate within a seeding time period.

In some embodiments, the series of acts 1500 further includes gelating the seeded cells by immersing the cell substrate and the seeded cells in a lobster saline solution.

The series of acts 1500 illustrated in FIG. 15 may include additional acts of combining cells of a first cell type and cells of a second cell type, wherein the first cell type and the second cell type comprise at least one of myocytes, adipocytes, or fibroblast; and suspending the combined cells in the alginate solution to form the cell mixture.

The series of acts 1500 may include an additional act of creating the alginate solution by: obtaining lobster media with a threshold level of calcium chloride; and adding sodium alginate to the lobster media.

In addition, or in alternative to, the series of acts 1400 in FIG. 14 or the series of acts 1500 in FIG. 15, this disclosure includes an apparatus for forming a structured porous cell substrate for growing cells. In some cases, the apparatus comprises a metal surface having a wettability gradient, a plastic cover, and an inlet for cell substrate solution intake. In certain embodiments, the plastic cover is covered with insulating material. Furthermore, in some implementations, the plastic cover comprises a bi-cylindrical plastic cover comprising multiple compartments. In some implementations, the bi-cylindrical plastic cover comprises two compartments shaped to resemble an abdomen or a tail of a lobster. In some embodiments, the plastic cover comprises a cylindrical plastic cover comprising a single compartment. Furthermore, in some embodiments, the plastic cover has silicone extensions spaced 5-8 mm apart.

Additionally, or alternatively, the disclosure includes a structured porous cell substrate for growing cells made by a process comprising steps of: injecting a cell substrate solution into a mold comprising a surface having a wettability gradient; cooling the surface of the mold to freeze the cell substrate solution, form a temperature gradient within the mold, and nucleate crystals; and sublimating the nucleated crystals in the frozen cell substrate solution to form a cell substrate. In some implementations, the structured porous cell substrate is made by the process further comprising steps of removing the frozen cell substrate from the mold prior to drying the frozen cell substrate solution. In some implementations, the mold comprises two semi-cylindrical compartments. Furthermore, in some examples, the mold comprises a cylindrical compartment. Additionally, in some embodiments, the mold comprises: a metal surface having the wettability gradient; and one or more additional plastic surfaces. Additionally, in some examples, cooling the surface of the mold comprises applying a cooling agent to the metal surface, wherein the cooling agent comprises at least one of dry ice or liquid nitrogen. Additionally, in one or more embodiments, the structured porous cell substrate is made by the process further comprising the steps of insulating the mold prior to cooling the surface of the mold by applying insulating materials to the one or more additional plastic surfaces of the mold. In some embodiments, the mold comprises rods to form pores in the structured porous cell substrate. In certain cases, the rods comprise silicone extensions. Accordingly, in certain embodiments, the mold comprises silicone extensions to form pores in the structured porous cell substrate.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absent a showing that the terms "first," "second," "third," etc., connote a specific order, these terms should not be understood to connote a specific order. Furthermore, absent a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The present invention may be embodied in other specific forms without departing from its spirit or essential characteristics. Indeed, the described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A method for forming a structured porous cell substrate for growing cells, the method comprising:
   injecting a cell substrate solution into a mold comprising a surface having a wettability gradient;
   cooling the surface of the mold to freeze the cell substrate solution, form a temperature gradient within the mold, and nucleate crystals;
   removing the frozen cell substrate solution from the mold;
   sublimating the nucleated crystals of the frozen cell substrate solution to form an edible cell substrate;
   seeding cells onto the edible cell substrate; and
   gelating the seeded cells by immersing the edible cell substrate and the seeded cells in a saline solution comprising a salt concentration between and including 5 g/L to 30 g/L.

2. The method of claim 1, wherein the mold comprises two semi- cylindrical compartments.

3. The method of claim 1, wherein the mold comprises a cylindrical compartment.

4. The method of claim 1, further comprising seeding cells onto the edible cell substrate by:
   suspending cells in an alginate solution to form a cell mixture;
   filling a container with the cell mixture and the edible cell substrate;
   sealing the container; and
   forcing the cell mixture through the edible cell substrate to seed cells throughout the edible cell substrate.

5. The method of claim 1, wherein the salt concentration is further between and including 10 g/L and 25 g/L.

6. The method of claim 1,
   wherein seeding cells onto the edible cell substrate comprises:
      flowing cells of a first cell type comprising at least one of myocytes, adipocytes, or fibroblasts through the edible cell substrate;

flowing cells of a second cell type comprising at least one of myocytes, adipocytes, or fibroblasts through the edible cell substrate; and wherein gelating the seeded cells comprises gelating seeded cells of the first cell type and seeded cells of the second cell type.

7. The method of claim 1, wherein the mold comprises:
a metal surface having the wettability gradient; and
one or more additional plastic surfaces.

8. The method of claim 7, further comprising cooling the surface of the mold by applying a cooling agent to the metal surface, wherein the cooling agent comprises at least one of dry ice or liquid nitrogen.

9. The method of claim 7, further comprising insulating the mold prior to cooling the surface of the mold by applying insulating materials to the one or more additional plastic surfaces of the mold.

10. The method of claim 1, wherein the mold comprises rods to form pores in the edible cell substrate.

11. The method of claim 10, wherein the rods comprise silicone extensions.

12. The method of claim 1, further comprising cross-linking the edible cell substrate and washing the edible cell substrate prior to seeding the cells onto the edible cell substrate.

13. The method of claim 12, further comprising heating the edible cell substrate at a cross-linking temperature for a heated period.

14. The method of claim 1, further comprising gelating the seeded cells by: incubating the seeded cells and the edible cell substrate at an incubation temperature for an incubation period.

15. The method of claim 1, further comprising forming a wettability gradient on the surface by treating an electrolytic cell with one or more electrodes producing a current for a wettability treatment period.

16. The method of claim 1, further comprising forming the temperature gradient by:
cooling the surface of the mold to a temperature between and including 0 C to -70 C; and
leaving an opposite surface of the mold at room temperature.

17. The method of claim 1, further comprising sublimating the nucleated crystals by freeze drying the frozen cell substrate for a freeze-drying period.

18. The method of claim 1, wherein the edible cell substrate comprises parallel-honeycomb tubes with a diameter of 200-500 μm.

19. The method of claim 1, wherein the edible cell substrate has pores of a size averaging between 40 and 60 micrometers in diameter.

* * * * *